(12) United States Patent
McCarthy et al.

(10) Patent No.: US 6,416,945 B1
(45) Date of Patent: Jul. 9, 2002

(54) VITRO METHOD FOR DISASSEMBLY/ REASSEMBLY OF PAPILLOMAVIRUS VIRUS-LIKE PARTICLES (VLPS)

(75) Inventors: Michael P. McCarthy, Poolesville; JoAnn Suzich, Washington Grove, both of MD (US)

(73) Assignee: Medimmune, Inc., Gaithersburg, MD (US)

( * ) Notice: Subject to any disclaimer, the term of this patent is extended or adjusted under 35 U.S.C. 154(b) by 0 days.

(21) Appl. No.: 09/379,615

(22) Filed: Aug. 24, 1999

Related U.S. Application Data

(62) Division of application No. 08/923,997, filed on Sep. 5, 1997, now abandoned.
(51) Int. Cl.$^7$ .............................. C12Q 1/70; C12N 7/00
(52) U.S. Cl. .................. 435/5; 435/235.1; 435/236; 435/239
(58) Field of Search .................. 435/5, 235.1, 236, 435/239; 935/65; 424/704.1

(56) References Cited

FOREIGN PATENT DOCUMENTS

WO          WO9915630          *  4/1999

OTHER PUBLICATIONS

Sapp et al. Journal of General Virology, 1995, vol. 76, pp. 2407–2412.*
Colomar et al . Journal of Virology, 1993, vol. 67 (5), pp. 27779–2786.*

* cited by examiner

Primary Examiner—Ali R. Salimi
(74) Attorney, Agent, or Firm—Robin L. Teskin

(57) ABSTRACT

A method of disassembly/reassembly of papillomavirus VLPs is provided. The resultant VLPs have enhanced homogeneity, present conformational, neutralizing PV epitopes, and therefore are useful prophylactic and diagnostic agents. Further, these VLPs can be used to encapsulate desired moieties, e.g., therapeutic or diagnostic agents, or "marker" DNAs, and the resultant VLPs used as in vivo delivery vehicles or as pseudovirions for evaluating vaccine efficacy.

9 Claims, 11 Drawing Sheets

Figure 1:
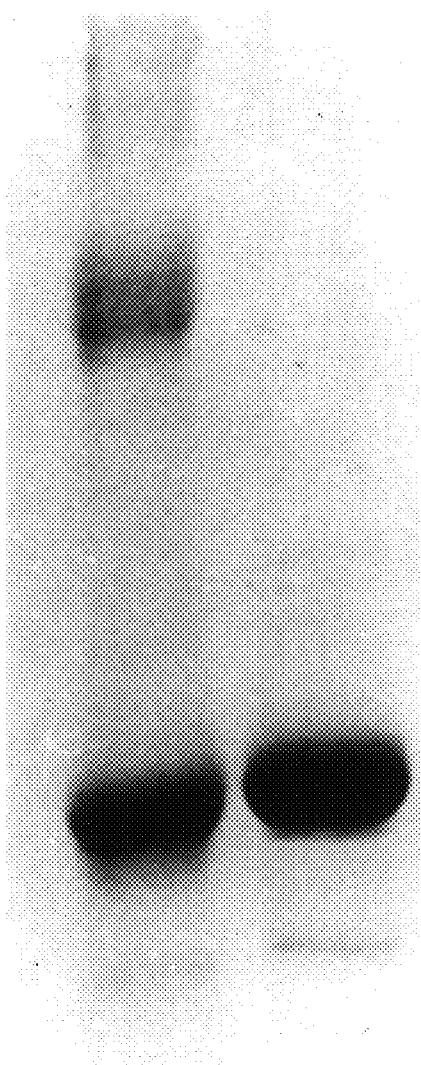

VITRO METHOD FOR DISASSEMBLY/REASSEMBLY OF PAPILLOMAVIRUS VIRUS-LIKE PARTICLES (VLPS)

This application is a divisional of application Ser. No. 08/923,997, filed Sep. 5, 1997 now abandoned.

FIELD OF THE INVENTION

The present invention provides a highly efficient means of disassembly of papillomavirus virus-like particles (VLPs) into capsomeres and/or smaller subunits, and reassembly into VLPs. These reassembled VLP-containing compositions produced by the invention express conformational, neutralizing epitopes and have high homogeneity and therefore comprise effective diagnostic and prophylactic agents for diagnosis or prevention of papillomavirus infection. Also, the present invention relates to the use of such VLPs for encapsulation of desired moieties, e.g., diagnostic or therapeutic agents, and the use thereof as "pseudovirions" for evaluating the efficacy of putative vaccines or therapeutics.

BACKGROUND OF THE INVENTION

Papillomaviruses infect a wide variety of different species of animals including humans. Infection is typically characterized by the induction of benign epithelial and fibro-epithelial tumors, or warts at the site of infection. Each species of vertebrate is infected by a species-specific set of papillomavirus, itself comprising several different papillomavirus types. For example, more than sixty different human papillomavirus (HPV) genotypes have been isolated. Papillomaviruses are highly species-specific infective agents. For example, canine and rabbit papillomaviruses cannot induce papillomas in heterologous species such as humans. Neutralizing immunity to infection against one papillomavirus type generally does not confer immunity against another type, even when the types infect a homologous species.

In humans, papillomaviruses cause genital warts, a prevalent sexually-transmitted disease. HPV types 6 and 11 are most commonly associated with benign genital warts condylomata acuminata. Genital warts are very common, and subclinical or inapparent HPV infection is even more common than clinical infection. While most HPV-induced lesions are benign, lesions arising from certain papillomavirus types, e.g., HPV-16 and HPV-18, can undergo malignant progression. Moreover, infection by one of the malignancy-associated papillomavirus types is considered to be a significant risk factor in the development of cervical cancer, the second most common cancer in women worldwide. Of the HPV genotypes involved in cervical cancer, HPV-16 is the most common, being found in about 50% of cervical cancers.

In view of the significant health risks posed by papillomavirus infection generally, and human papillomavirus infection in particular, various groups have reported the development of recombinant papillomavirus antigens and their use as diagnostic agents and as prophylactic vaccines. In general, such research has been focused toward producing prophylactic vaccines containing the major capsid protein (L1) alone or in combination with the minor capsid protein (L2). For example, Ghim et al, Virology, 190:548–552 (1992), reported the expression of HPV-1 L1 protein, using a vaccinia expression in Cos cells, which displayed conformational epitopes and the use thereof as a vaccine or for serological typing or detection. This work is also the basis of a patent application, U.S. Ser. No. 07/903,109, filed Jun. 25, 1992 (abandoned in favor of U.S. Ser. No. 08/216,506, filed on Mar. 22, 1994), which has been licensed by the assignee of this application. Also, Suzich et al, Proc. Natl. Acad. Sci., U.S.A., 92:11553–11557 (1995), report that the immunization of canines with a recombinant canine oral papillomavirus (COPV) expressed in a baculovirus/insect cell system completely prevented the development of viral mucosal papillomas. These results are important given the significant similarities between many HPVs and COPV. For example, COPV, similar to HPVs associated with anogenital and genital cancer, infects and induces lesions at a mucosal site. Also, the L1 sequences of COPV shares structural similarities to HPV L1 sequences. Given these similarities, the COPV/beagle model is useful for investigation of L1 protein-containing vaccines, e.g., investigation of the protective immune response, protection from natural infection and optimization of vaccination protocols. (Id.)

Also, a research group from the University of Rochester reported the production of human papillomavirus major capsid protein (L1) and virus-like particles using a baculovirus/insect cell expression system (Rose et al, University of Rochester, WO 94/20137, published on Sep. 15, 1994). In particular, they reported the expression of the L1 major capsid protein of HPV-6 and HPV-11 and the production of HPV-6, HPV-11, HPV-16 and HPV-18 virus-like particles.

Further, a University of Queensland research group also purportedly disclosed the recombinant manufacture of papillomavirus L1 and/or L2 proteins and virus-like particles as well as their potential use as vaccines (Frazer et al, WO 93/02189, published Feb. 4, 1993).

Still further, a United States government research group reported recombinant papillomavirus capsid proteins purportedly capable of self-assembly into capsomere structures and viral capsids that comprise conformational antigenic epitopes (U.S. Pat. No. 5,437,951, Lowy et al, issued Aug. 1, 1995). The claims of this patent are directed to a specific HPV-16 DNA sequence which encodes an L1 protein capable of self-assembly and use thereof to express recombinant HPV-16 capsids containing said HPV-16 L1 protein.

With respect to HPV capsid protein containing vaccines, it is widely accepted by those skilled in the art that a necessary prerequisite of an efficacious HPV L1 major capsid protein-based vaccine is that the L1 protein present conformational epitopes expressed by native human papillomavirus major capsid proteins (see, e.g., Hines et al, Gynecologic Oncology, 53:13–20 (1994); Suzich et al, Proc. Natl. Acad. Sci., U.S.A., 92:11553–11557 (1995)).

Both non-particle and particle recombinant HPV L1 proteins that present native conformational HPV L1 epitopes have been reported in the literature. It is known that L1 is stable in several oligomeric configurations, e.g., (i) capsomeres which comprise pentamers of the L1 protein and (ii) capsids which are constituted of seventy-two capsomeres in a T=7 icosahedron structure. Also, it is known that the L1 protein, when expressed in eukaryotic cells by itself, or in combination with L2, is capable of efficient self-assembly into capsid-like structures generally referred to as virus-like particles (VLPs).

VLPs have been reported to be morphologically and antigenically similar to authentic virions. Moreover, immunization with VLPs has been reported to elicit the production of virus-neutralizing antibodies. More specifically, results with a variety of animal papillomaviruses (canine oral papillomavirus and bovine papillomavirus-4) have suggested that immunization with VLPs results in protection against subsequent papillomavirus infection. Consequently VLPs composed of HPV L1 proteins have been proposed as vaccines for preventing diseases associated with human papillomavirus infections.

For example, it has been reported that the L1 protein can assemble into VLPs when expressed using recombinant baculovirus and vaccinia virus vectors and in recombinant yeast (Hagensee et al, *J. Virol.*, 68:4503–4505 (1994); Hofmann et al, *Virology*, 209:506–518 (1995); Kirnbauer et al, *Proc. Natl. Acad. Sci. USA*, 89:12180–12184 (1992); Kirnbauer et al, *J. Virol.*, 67:6929–6936 (1993); Rose et al, *J. Virol.*, 67:1936–1944 (1993); Sasagawa et al, *Virology*, 206:126–135 (1995); Suzich et al, *Proc. Natl. Acad. Sci. USA*, 92:11553–11557 (1995); Volpers et al, *Virology*, 200:504–512 (1994); Zhou et al, *J. Virol.*, 68:619–625 (1994)).

Most previous recombinant L1 preparations isolated from eukaryotic cells have resulted in a variable population of VLPs approaching 55 nm in diameter, which are similar in appearance to intact virions. However, VLP assembly is somewhat sensitive to cell type. For example, L1 expressed in *Escherichia coli* is expressed largely in the form of capsomeres or smaller, with few or no capsids apparent either in the cell or upon purification (Rose et al, *J. Virol.*, 67:1936–1944 (1993); Li et al, *J. Virol.*, 71:2988–2995 (1997)). Similar results are observed when the polyoma virus VP1 protein is expressed in *E. coli* (Salunke et al, *Biophys. J.*, 56:887–900 (1989)).

To date there has not been reported an effective in vitro method for the quantitative disassembly and subsequent reassembly of papillomavirus VLPs. Such a method would be highly advantageous as it would potentially enable the preparation of more stable and/or homogeneous papillomavirus VLPs. This would be beneficial as homogeneity and stability are both significant concerns in vaccine preparation and characterization during manufacture. Furthermore, the ability to disassemble and reassemble VLPs has important applications to VLP purification. HPV L1 proteins expressed in eukaryotic cells spontaneously assemble to form VLPs, as discussed above. However, most protein purification prodecures have been designed to purify proteins much smaller than the ~20 million dalton, 55 nm VLP. The potential to disassemble VLPs extracted from eukaryotic cells to the level of L1 capsomeres or smaller, purify the smaller components by conventional techniques, and then reassemble to form VLPs at the desired stage of the purification process is very powerful, and is currently being utilized in the purification of HPV-$16_{Tr}$ VLPs, as discussed below (composed of a mutated form of the HPV-16 L1 protein from which the C-terminal 34 amino acids have been deleted). Finally the ability to disassemble and reassemble VLPs in vitro allows for the packaging of desired exogenous compounds within the reassembled VLP.

Earlier attempts at papilloma VLP disassembly have included experiments based on earlier work performed on polyomavirus, a related papovarirus, wherein it was shown that both the reduction of disulfides and chelation of cations were essential for virion disassembly (Brady et al, *J. Virol.*, 23:717–724 (1977)). However, in the case of HPV VLPs it has been shown that the low levels of reducing agent (1–10 mM DTT) which provide for optimal polyomavirus disassembly in the presence of low levels of chelating agents (e.g., 0.5–10 mM EGTA) were only slightly effective at disassembly of papillomavirus VLPs (see Table 1, Li et al, *J. Virol.*, 71:2988–2995 (1997)). By contrast, partially trypsinized HPV-11 L1 VLPs have been reported to disassociate effectively under such conditions (Li et al, *J. Virol.*, 71:2988–2995 (1997)). However, this is disadvantageous as the use of protease may result in adverse effects, e.g., removal of neutralizing epitopes.

Also, Sapp and coworker demonstrated that "partial disassembly" of HPV-33 VLPs could by achieved by treatment with reducing agent alone (20 mM DTT). However, the extent of VLP breakdown was not determined (Sapp et al, *J. Gen. Virol.*, 76:2407–2412 (1995)).

As discussed above, HPV capsid assembly requires correctly-folded L1 protein. However, additional factors significant for VLP formulation and stability have not been well elucidated. With respect thereto, it is generally known that VLP assembly can be affected by numerous factors. For example, factors and conditions known to affect assembly for other viruses include, by way of example: pH, ionic strength, post-translational modifications of viral capsid proteins, disulfide bonds, and divalent cation bonding, among others. For example, the importance of cation bonding, specifically calcium, in maintaining virion integrity has been shown for polyomavirus (Brady et al, *J. Virol.*, 23:717–724 (1977)), and rotovirus (Gajardo et al, *J. Virol.*, 71:2211–2216 (1997)). Also, disulfide bonds appear to be significant for stabilizing polyomavirus (Walter et al, *Cold Spring Har. Symp. Quant. Biol.*, 39:255–257 (1975); Brady et al, *J. Virol.*, 23:717–724 (1977); and SV40 viruses (Christansen et al, *J. Virol.*, 21:1079–1084 (1977)). Also, it is known that factors such as pH and ionic strength influence polyomavirus capsid stability, presumably by affecting electrostatic interactions (Brady et al, *J. Virol.*, 23:717–724 (1977); Salunke et al, *Cell*, 46:895–904 (1986); Salunke et al, *Biophys. J.*, 56:887–900 (1980)). Also, it is known that post-translational modifications of some viral capsid proteins may affect capsid stability and assembly, e.g., glycosylation, phosphorylation, and acetylation (Garcea et al, *Proc. Natl. Acad. Sci. USA*, 80:3613–3617 (1983); Xi et al, *J. Gen. Virol.*, 72:2981–2988 (1991)). Thus, there are numerous interrelated factors which may affect capsid stability, assembly and disassembly which vary widely even for related viruses.

Therefore, there exists a need in the art for elucidation of the factors that affect papillomavirus VLP assembly and disassembly. Moreover, based thereon, there exists a need in the art for an efficient in vitro method of disassembly and reassembly of papillomavirus VLPs which results in VLPs having good homogeneity, stability, and immunogenic properties, i.e., those which present conformational and more particularly neutralizing epitopes expressed on the surface of native, intact papillomavirus virions. Moreover, there is a significant need for methods for disassembly and reassembly of papillomavirus VLPs which obviate the problems of partial VLP disassembly and which avoid the use of protease used in prior methods of generating papillomavirus VLPs.

OBJECTS OF THE INVENTION

Thus, it is an object of the invention to solve the problems of the prior art.

More specifically, it is an object of the invention to provide a novel method for disassembly and reassembly of papillomavirus VLPs.

Still more specifically, it is an object of the invention to provide a novel method for disassembly and reassembly of human papillomavirus VLPs.

It is also an object of the invention to provide a method which enables quantitative disassembly and assembly of papillomavirus VLPs in large quantities.

It is another object of the invention to provide papillomavirus VLP-containing compositions, preferably human papillomavirus VLP-containing compositions, of improved quality, e.g., improved homogeneity, immunogenicity, and/or stability.

It is another object of the invention to provide an improved means of VLP purification by incorporating VLP disassembly/reassembly within the purification process.

It is still another object of the invention to provide a method for encapsulating desired moieties in papillimavirus VLPs, e.g., therapeutic or diagnostic agents.

It is another object of the invention to provide papillomavirus VLPs, preferably human papillomavirus VLPs, which contain desired therapeutic or diagnostic agents contained therein, e.g., anti-cancer agents or antiviral agents.

It is still another object of the invention to generate "pseudovirions" for HPV virus types wherein recoverable quantities of HPV virions are not currently available by the encapsulation of exogenous compounds into HPV VLPs constructed using L1 and L1/L2 proteins of said HPV papillomavirus, in particular a DNA corresponding to the genome of said HPV or a fragment thereof, or a DNA encoding a selectable marker such as β-galactosidase.

It is still another object of the invention to provide a novel method of delivery of a desired moiety, e.g., a DNA to desired cells wherein the delivery vehicle for such moiety, e.g., sense or antisense DNA, comprises a papillomavirus VLP.

It is still another object of the present invention to use pseudovirions based on HPV VLPs in an in vitro assay for assaying the efficacy of potential HPV vaccines which assays the ability of neutralizing antibodies to inhibit the insertion of a DNA encapsulated therein into cells normally infected by said HPV.

BRIEF DESCRIPTION OF THE INVENTION

Therefore, the invention generally relates to a novel method for disassembly and reassembly of papillomavirus VLPs, preferably human papillomavirus VLPs in vitro.

As discussed above, papillomavirus VLPs are constituted primarily of a structural protein L1, which is stable as pentameric capsomeres or capsids composed of 72 capsomeres. Such VLPs may also comprise the L2 protein. In particular, by the judicious choice of experimental conditions, the present inventors have surprisingly discovered that quantitative disassembly of papillomavirus VLPs (almost entirely to the level of capsomeres or smaller), and subsequent reassembly can be consistently achieved by prolonged exposure of VLPs, to a solution comprising a high concentration of at least one sulfhydryl reducing agent preferably contained in moderate to low ionic strength buffers. Specifically, the subject method results in reassembled VLP-containing compositions of very high homogeneity, predominantly comprising particles in the range of full-size VLPs, averaging 56.5±7.0 nm (n=15) with very few partially assembled VLPs or smaller complexes. The yields are also very high, i.e., quantitative, averaging 80–90% in terms of total L1 protein from starting material to reassembled VLPs under optimal disassembly conditions. Moreover, essentially all the previously disassociated capsomeres reassemble to produce soluble, filterable, full-size VLPs.

It has been unexpectedly found that use of such conditions results in papillomavirus VLP compositions of enhanced homogeneity (relative to VLP starting material and to available VLP compositions), i.e., homogeneous compositions constituted almost entirely of papillomavirus VLPs which are 55 nm, 150 S. Further, it has been shown that these homogeneous VLPs present conformational, neutralizing HPV epitopes, a prerequisite of an effective prophylactic HPV VLP-based vaccine. Also, it has been surprisingly found by the inventors that chelators do not enhance VLP disassembly, and moreover may inhibit reassembly of capsomeres into VLPs. As discussed in greater detail infra, these findings were surprising because for a related papovavirus, polyomavirus, it has been shown that both exposure to low levels of sulfhydryl reducing agent and chelation of calcium ions were essential for virion disassembly. By contrast, such conditions are only slightly effective for disassembly of papilloma VLPs.

As noted, it has also been found that the papillomavirus capsomere and VLP compositions, produced according to the invention present structure-specific (conformational), in particular neutralizing epitopes found on the surface of intact papillomavirus virions. This has been demonstrated both by their reactivity with neutralizing and structure-specific anti-L1 papillomavirus monoclonal antibodies in an ELISA assay and by their ability to induce the synthesis of antibodies which neutralize papillomavirus virus infection in an RT-PCT infection assay. Therefore, they are well suited for use as prophylactic agents for preventing PV infection and for diagnostic purposes. Furthermore, the subject methods for VLP disassembly and reassembly can be applied at different degrees of VLP purity. This allows for disassembly of crude mixtures of VLPs, purification of the smaller, soluble VLP components (which is simpler due to their greatly diminished size), followed by reassembly at the desired stage of the purification process.

Also, as discussed in greater detail infra, the subject methods further provide for the introduction of desired moieties, e.g., DNAs, proteins, peptides, hormones, radionuclides, anti-cancer agents and antiviral agents into VLPs during reassembly. This is advantageous as such VLPs may be used as delivery vehicles (for insertion of desired moieties into cells) and as "pseudovirions" for evaluating the prophylactic efficacy of papillomavirus vaccines.

The present inventors hypothesize that papillomavirus VLP disassembly requires prolonged exposure to very high levels of reducing agent because of the presence of stabilizing disulfide bonds which likely are buried and inaccessible, and that exposure of these bonds to solvent by local structural fluctuations is very infrequent. (This phenomenon is discussed in greater detail in application Ser. No. 08/888,050 filed on Jul. 3, 1997.) Apparently, upon prolonged exposure at high reducing agent concentrations and at low to moderate ionic strength, these bonds become accessible over time.

Definitions:

Major capsid protein or L1 protein

This refers to the structural protein of papillomavirus (PV) which constitutes the major portion of the PV capsid structure. This protein has reported application in the preparation of HPV vaccines and as a diagnostic agent.

Minor capsid protein or L2 protein

This refers to the structural protein of papillomavirus which constitutes a minor portion of the PV viral capsid structure.

Virus-like particles or VLPs

This refers to the capsid-like structures which result upon expression and assembly of a papillomavirus L1 DNA sequence alone or in combination with an L2 DNA sequence. VLPs are morphologically and antigenically similar to authentic virions. VLPs may be produced in vivo, in suitable host cells, e.g., mammalian and insect host cells, or may form spontaneously upon purification of recombinant L1 proteins.

Pseudovirion

This refers to VLPs, containing exogenous marker compounds, composed of L1 or L1 and L2 proteins of a specific PV type. Pseudoviriouns can be used to test the efficacy of substances, such as antibodies, to block specific viral binding and/or uptake into target cells in cases where authentic virus is not available.

Correctly-folded L1 protein

This refers to L1 protein, (either monomeric, in the form of small oligomers (dimers-tetramers) or capsomeres), which is in a conformation suitable for reassembly into VLPs and which retains epitopes present on viral capsids or VLPs.

Capsomeres

This refers to an oligomeric configuration of the L1 protein which is constituted of L1 pentamers.

Capsids

This refers to the structural portion of the papillomavirus which is comprised of capsomeres. More specifically, it is constituted of seventy-two capsomeres in a T=7 icosahedron structure.

Conformational L1 HPV Epitope

This refers to an epitope expressed on the surface of correctly-folded L1 protein which is also expressed by an L1 protein of a corresponding wild-type, infectious HPV. It is well accepted by those skilled in the art that the presentation of conformational epitopes is essential to the efficacy (both as prophylactic and diagnostic agents) of HPV L1 protein immunogens.

Conformational Neutralizing L1 HPV Epitope

This refers to an epitope expressed on the surface of correctly-folded L1 protein which is also expressed by an L1 protein of a corresponding wild-type, infectious HPV, and which elicits neutralizing antibodies. It is well accepted by those skilled in the art that the presentation of conformational neutralizing epitopes is essential to the efficacy (both as prophylactic and diagnostic agents) of HPV L1 protein immunogens.

Conformational Antibody

This refers to an antibody that specifically binds an epitope expressed on correctly-folded L1 protein but not on denatured L1 protein.

Reducing Agent Solution of High Concentration

This refers to a solution containing an amount of at least one sulfhydryl reducing agent, e.g., glutathione, β-mercaptoethanol or dithiothreitol which provides for at least 70% disassembly of papillomavirus VLPs, when VLPs are contacted therewith for prolonged periods, typically at least 2 hours, and more preferably at least 16 hours. The concentration of the reducing agent may vary dependent upon the particular reducing agent. In the case of β-mercaptoethanol, this amount will preferably be at least 1% by weight, more preferably at least 3–5% by weight. In the case of dithiothreitol, the amount will preferably be at least about 100 mM.

Prolonged Exposure or Contacting of VLPs with Reducing Agent Solution of High Concentration This refers to the time that VLPs are contacted with reducing agent solution of high concentration that is sufficient to provide for at least 70% disassembly of VLPs into capsomeres. Preferably, such prolonged exposure will result in 70–90% disassembly and optimally virtually total VLP disassembly. This time will vary for different PV types, and may also depend upon the cells that VLPs are expressed (starting material), degree of purity (presence or absence of aggregates), pH, and ionic strength. Additionally, VLPs formed from mutated or chemically-altered L1 protein, e.g., C-terminally truncated L1 protein, may disassemble under milder conditions. Generally, this exposure will be for at least 2 hours (in the case of HPV-$16_{T_r}$ VLPs), and more typically longer, i.e., at least 12 hours, more preferably at least 16 hours (in the case of HPV-11 VLPs).

DETAILED DESCRIPTION OF FIGURES

FIG. 1: SDS/PAGE analysis of purified HPV-11 L1 protein. The protein was mixed with sample preparation buffer in the absence (lane 1) or presence (lane 2) of 2 mM DTT and boiled for 2 minutes prior to gel electrophoresis. Shown on the left are the positions at which molecular weight standards (in Da×$10^{-3}$) migrated.

Figure 2:
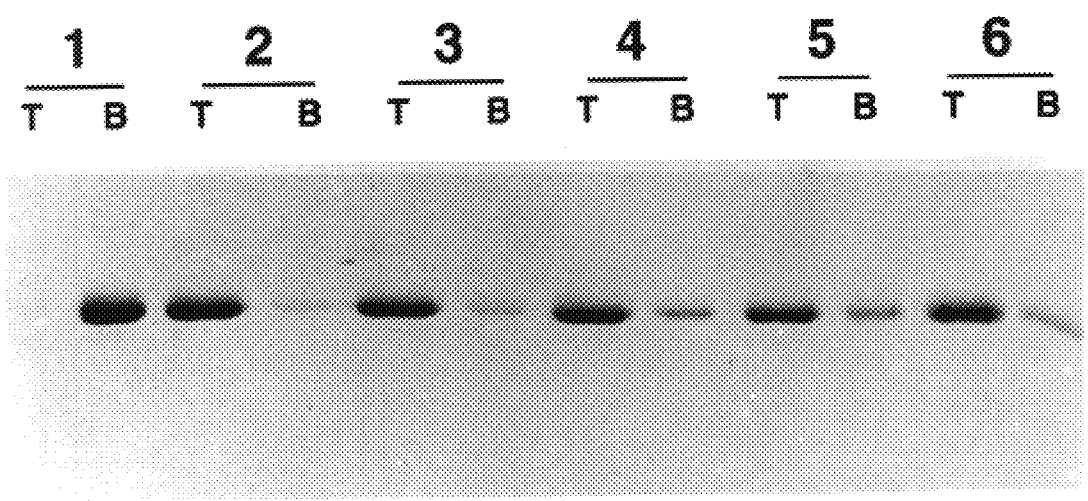

FIG. 2: 30% sucrose cushion analysis of HPV-11 VLP disassembly. HPV-11 preparations were treated at 4° C. as described in the text, and samples were taken at the top (T) or bottom (B) of the sucrose cushion prior to gel electrophoresis. Group 1, untreated, purified HPV-11 VLP starting material in PBS. Group 2, VLPs incubated with 5% βME for 16 hours. Group 3, VLPs incubated with 5% βME for 1 hour. Group 4, VLPs incubated with 2% βME for 16 hours. Group 5, VLPs incubated with 0.5% βME for 16 hours. Group 6, VLPs incubated with 10 mM DTT, 5 mM EDTA for 16 hours.

FIG. 3: 5–20% linear sucrose gradient analysis of disassembled HPV-11 VLPs. VLPs in PBS were incubated with 5% βME (a), or 200 mM NaHCO$_3$, pH 9.6(b) for 16 hours at 4° C. and then centrifuged on a 5–20% linear sucrose gradient as described in the text. The gradient was collected in 25 fractions (0.5 ml), and the pellet (P) was resuspended in 0.5 ml PBS. Shown is an immunoblot demonstrating the position of the L1 protein across the gradient. Also indicated are the peak positions at which sedimentation standards migrated when run on separate gradients.

FIG. 4: 10–65% linear sucrose gradient analysis of HPV-11 VLPs in various states of assembly. An aliquot of purified VLP starting material (a) was incubated with 5% βME for 16 hours at 4° C.(b). A portion of βME-treated VLPs were then reassembled by dialysis into PBS-0.5 NaCl to remove reducing agent (c). The samples are then centrifuged on 10–65% linear sucrose gradients as described in the text. Each gradient was collected in 12 fractions (1 ml), and the pellet (P) was resuspended in 1 ml PBS. Shown are immunoblots demonstrating the positions at which the L1 protein migrated on the different gradients. Also indicated are the peak positions at which sedimentation standards migrated, as in FIG. 3.

FIG. 5: Electron micrographs of HPV-11 VLPs in various states of assembly. VLPs, treated as described, were stained with 2% phosphotungstic acid, applied to grids, and photographed at magnifications of 15–25,000 times. a, purified VLP starting material, b, VLPs disassembled to the level of capsomeres by incubation with 5% βME for 16 hours at 4° C. c, VLPs reassembled from disassembled VLPs by dialysis into PBS-0.5 NaCl, d, the central region of image c at greater magnification. Scale bar: a,c=200 nm; b,d,=100 nm.

FIG. 6: Reaction of intact and disassembled VLPs with HPV-11 structure-specific monoclonal antibodies. HPV-11

L1 VLP starting material (A), VLPs disassembled by treatment with 5% βME either without (B) or with (C) subsequent dialysis into PBS-0.5 M NaCl to remove reducing agent, and VLPs disassembled in the presence of 200 mM carbonate, pH 9.6 and then dialyzed into PBS-0.5 M NaCl (D) were attached to the wells of microtiter plates. HPV-11 structure-specific monoclonal antibodies H11.F1 (HPV-11 neutralizing; V) and H11.A3 (HPV-11 non-neutralizing; ●) were tested for immunoreactivity to the bound antigens in an ELISA as described in the Materials and Methods. Reactivity with monoclonal antibody AU1 (■), which recognizes a linear epitope found on HPV-11 L1, was used as a control to demonstrate antigen attachment to the microtiter wells.

Figure 7A:
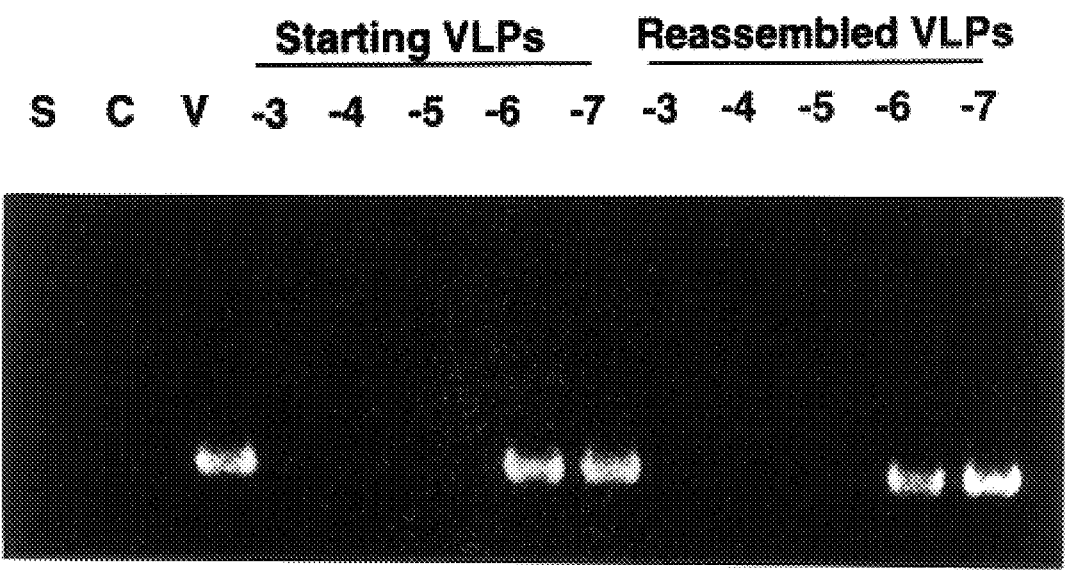
Figure 7B:
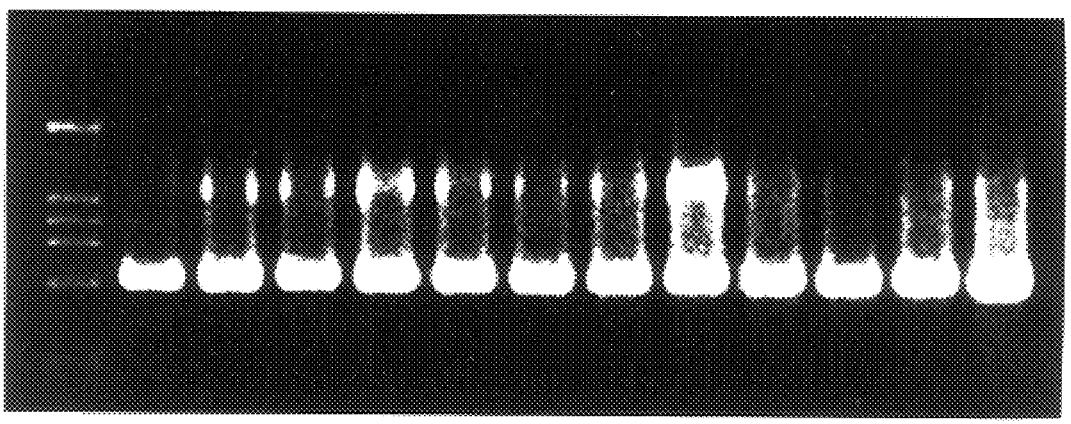

FIG. 7: Comparison of the ability of antisera raised against initial purified HPV-11 VLPs, and reassembled VLPs, to neutralize HPV-11 virus. Anti-HPV-11 sera were incubated with HPV-11 virions for 60 min at 37° C. before addition to HaCaT cells. Alternatively, virions were added to cells without pre-incubation with serum. Six days post-infection, the cells were harvested and total RNA was extracted. Ten percent of the total RNA was used for reverse transcription, and ten percent of the resulting cDNA was then used as template for nested PCR using primers specific for the HPV-11 E1∧E4 spliced message. PCR products were separated on 2% agarose gels. Gels were stained with ethidium bromide and examined under UV light for the presence of the ~0.6 kb E1∧E4 band (a). PCR amplification of β-actin was performed on all cDNA samples as an internal control (b). The expected size of the β-actin band is ~0.6 kb. Lane S contains molecular size markers. Lane C represents reactions carried out with RNA from cells incubated without virus and Lane V represents cells incubated with virus that had not been pre-incubated with serum. As expected, the E1∧E4 band is detected in virus-infected but not in uninfected cells. The next lanes contain PCR products from cells infected with virus that had been pre-incubated with serial $\log_{10}$ dilutions of anti-HPV-11 antiserum ($10^{-3}$–$10^{-7}$) raised against initial purified HPV-11 VLPs and reassembled VLPs as indicated.

Figure 8:
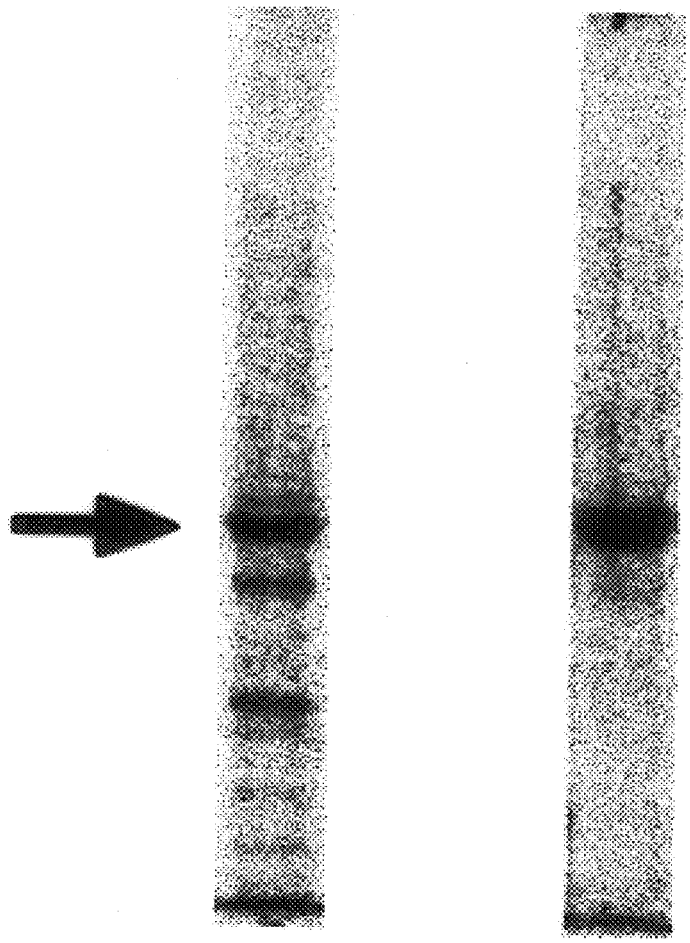

FIG. 8: SDS/Page comparison of HPV-16$_{Tr}$ VLPs in the assembled (−βME) and disassembled (+βME, Run 2) states, indicating the greater purity of VLPs purified in the disassembled state. The position at which HPV-16$_{Tr}$ L1 protein migrates is indicated by the arrow.

Figure 9:
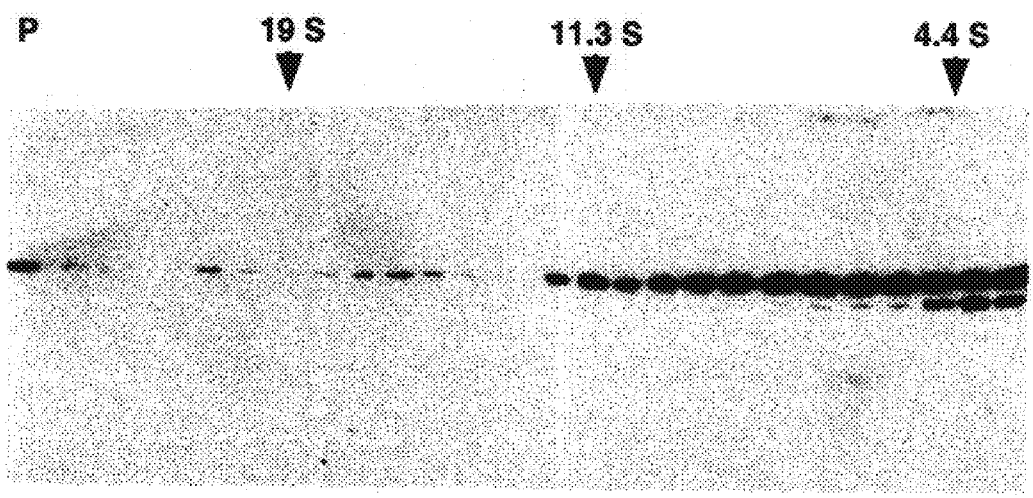

FIG. 9: 5–20% linear sucrose gradient analysis of disassembled HPV-16$_{Tr}$ VLPs. Final purified +βME Run 2 VLPs (see Table 3) in PBS were incubated with 4% βME for 16 hours at 4° C. and then centrifuged on a 5–20% linear sucrose gradient as described in the Methods section. The gradient was collected in 25 fractions (0.5 ml), and the pellet (P) was resuspended in 0.5 ml PBS. Shown is an immunoblot, probed with the HPV-16 specific monoclonal antibody 16-E, demonstrating the position of the L1 protein across the gradient. Also indicated are the peak positions at which sedimentation standards migrated when run on separate gradients.

Figure 10A:
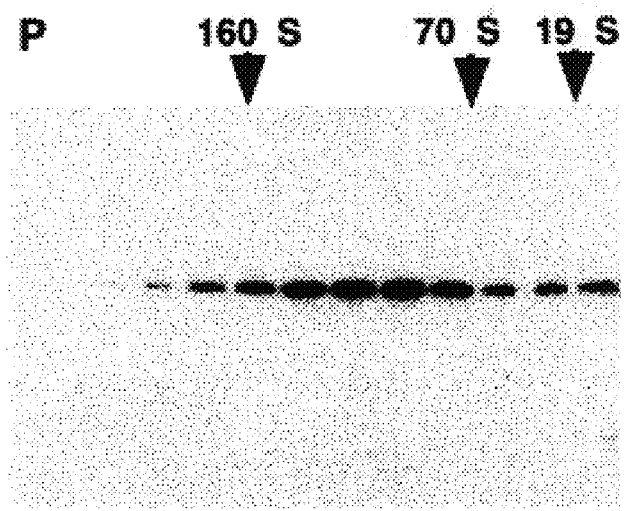
Figure 10B:
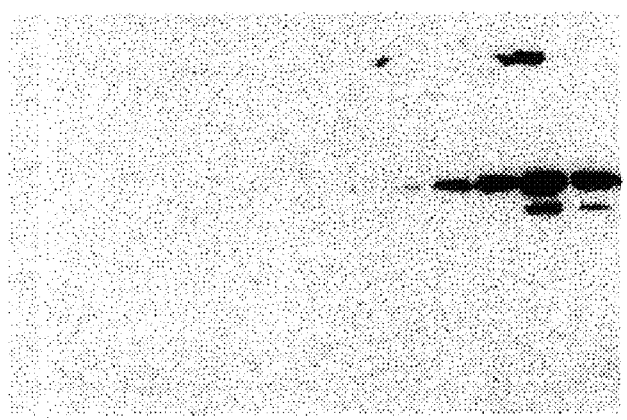
Figure 10C:
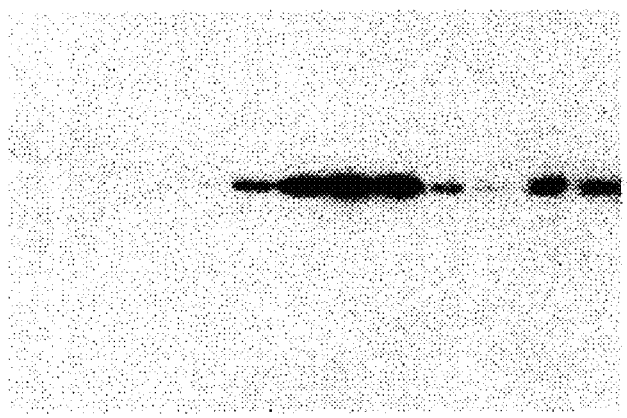

FIG. 10: 10–65% linear sucrose gradient analysis of HPV-16$_{Tr}$ VLPs in various states of assembly. An aliquot of (a) purified VLP starting material (+βME Run 2; see Table 3) was incubated with 4% βME for 16 hours at 4° C. (b). A portion of βME-treated VLPs were then reassembled by dialysis into PBS-0.5 NaCl to remove reducing agent (c). The samples were then centrifuged on 10–65% linear sucrose gradients as described in the text. Each gradient was collected in 12 fractions (1 ml), and the pellet (P) was resuspended in 1 ml PBS. Shown are immunoblots, probed with the HPV-16 specific monoclonal antibody 16-E, demonstrating the positions at which the L1 protein migrated on the different gradients. Also indicated are the peak positions at which sedimentation standards migrated, as in FIG. 9.

DETAILED DESCRIPTION OF THE INVENTION

As discussed, the present invention generally relates to a novel method which provides for highly effective disassembly of papillomavirus VLPs, i.e., at least 70% disassembly, more preferably 70–90% disassembly, and most preferably total VLP disassembly, which comprises prolonged exposure of papillomavirus VLPs comprised of L1 or a combination of L1 and L2 proteins to a sulfhydryl reducing agent solution of high concentration. In general, the concentration of the reducing agent will be at least 1% by weight, and more preferably about 3–5% by weight, wherein the reducing agent-containing solution preferably has an ionic strength which is at most about 0.5 and preferably lower.

However, reducing agent concentrations and ionic strength may vary for different papillomavirus types, the host cells they are obtained from, mutated and/or chemically-altered forms of the L1 protein, and purity. More specifically, the present inventors have elucidated conditions for maximal disassembly of purified VLPs in vitro, which provides for efficient subsequent reassembly. It has been discovered that prolonged incubation of papillomavirus VLPs with relatively high concentrations of reducing agents at ionic strengths which are at most 0.5 M, and more preferably around physiological ionic strength or less, is both necessary and sufficient to generate homogeneous soluble capsomeres from purified VLPs. Moreover, it has been found that upon removal or alternatively by oxidation of the reducing agent, a defined population of intact, appropriately-sized VLPs is obtained.

This has been shown in particular using HPV-11 VLPs produced in a baculovirus/insect cell system, i.e., in *Trichoplasia ni* (High Five®) cells infected with a recombinant baculovirus containing the entire HPV-11 L1 DNA sequence. However, based on these results, it is reasonable to conclude that similar results will be achieved using papillomavirus VLPs produced from other types and species, in particular other human papillomavirus types. This is reasonable as numerous papillomavirus L1 proteins have been demonstrated to result in VLPs when expressed in suitable recombinant expression vector systems.

Likewise, it is reasonable to expect that similar results will be achieved using papillomavirus VLPs comprised of a combination of L1 and L2 proteins, as they appear virtually identical to VLPs made only of L1 proteins. [However, assuming that L2 has a significant stabilizing role, the present inventors acknowledge that disassembly may require the use of higher concentrations of reducing agent, more prolonged exposure thereto, elevated pH and/or reduced ionic strength during disassembly.] Moreover, it is expected that the subject methods will be suitable for disassembly/assembly of VLPs obtained from any host cell system that results in the production of papillomavirus VLPs. While Applicants acknowledge that there exists some host cell differences, as discussed supra, many host cells have been reported to express papillomavirus VLPs in the form of VLPs.

In general, the desired VLP starting material will be produced in a suitable host cell system, e.g., a baculovirus/insect cell system, and extracted therefrom using known methods. The extraction technique will depend upon factors such as the specific host cells used, concentration, whether protein remains intracellular or is secreted, among other factors.

Disassembly of the VLPs can be performed at different levels of VLP purity. When performed in conjunction with purification, VLPs will be extracted from cells, disassembled, purified by conventional techniques, and reassembled at the desired degree of purity. In the cases where VLPs will be used to package exogenous compounds, or when disassembly/reassembly is performed to improve the homogeneity of the final product, the VLPs used will be of fairly high purity. In these instances, the VLPs used for disassembly will preferably be at least 10–30% by weight, more preferably 50% by weight, and most preferably at least 70–90% by weight. Methods of determining VLP purity are well known and include SDS-PAGE densitometric methods.

As discussed in detail infra in the materials and methods section, the present inventors developed a rapid screening assay for the study of VLP disassembly which uses a sucrose gradient system. In this system, intact VLPs pellet through a 30% sucrose cushion, whereas nonaggregated capsomeres, smaller L1 oligomers or L1 monomers remain on top of the cushion. Therefore, this assay method is beneficial as it facilitates the precise identification of conditions that result in maximal VLP disassembly.

In general, it was found that maximal VLP disassembly requires prolonged exposure of non-aggregated VLPs to a solution containing a high concentration of sulfhydryl reducing agent. As explained previously, prolonged exposure is the duration sufficient to result in at least 70% disassembly of VLPs, more preferably 70–90% VLP disassembly, and ideally virtually total VLP disassembly. In the case of recombinant HPV-11 L1 VLPs produced in the exemplified insect cell system, maximal disassembly occurred after about 16 hours at 4° C. (using a solution containing 5% by weight of β-mercaptoethanol). However, such exposure times may potentially be reduced using other VLP starting materials, different pH conditions, higher reducing agent concentrations, and lower ionic strengths. For example, it has been found [results not shown] that substantial disassembly of VLPs formed by a C-terminally-truncated form of the HPV-16 L1 protein can be effected by exposure of such VLPs with a β-mercaptoethanol solution (4%) after about 2 hours at 4° C.

The subject VLP disassembly method has been demonstrated to be effective using β-mercaptoethanol and dithiothreitol as the reducing agents. However, it is expected that other known reducing agents should provide similar results. Examples of suitable reducing agents useful in the invention include glutathione, β-mercaptoethanol, dithiothreitol, dithioerythritol, cysteine, hydrogen sulfide and mixtures thereof.

As noted, the present method contacts VLPs with a solution having a high sulfhydryl reducing agent concentration. Herein, this is defined to be a reducing agent concentration that results in substantial disassembly of VLPs, i.e., at least 70%, preferably at least 70–90%, and more preferably virtually total VLP disassembly, after prolonged exposure.

These high reducing agent concentrations will vary dependent upon the particular reducing agents or combination. In the case of β-mercaptoethanol, it has been found that a concentration of at least about 5% by weight (713 mM) results in optimal HPV-11 L1 VLP disassembly at physiological ionic strength. Lower concentrations of reducing agent and reduced exposure periods result in less effective VLP disassembly. For example, it has been found that 4% β-mercaptoethanol solutions also provide for effective disassembly (at Least 70%).

It has also been found that the ionic strength is an important parameter in the disassembly method. Preferably, disassembly will be effected using a solution having an ionic strength which is at most 0.5, and preferably lower, more preferably disassembly will be effected at about "physiological" ionic strength (i.e., 0.15 NaCl) or lower. It has been found that higher ionic strengths render the VLP disassembly method less effective. In general, ionic strength will be at most about 0.5, more preferably at most about 0.25, and most preferably at most about 0.15.

It was also discovered that the presence of VLP aggregation has adverse effects on disassembly. This effect may be avoided by removal of aggregated material, or potentially may be obviated by more prolonged exposure of the VLPs to the high concentration reducing agent solution. This likely occurs because the disulfide bonds are buried and thus inaccessible to reducing agent in aggregates, thereby preventing disassembly.

Also, as discussed, it has been surprisingly found that chelators, even at high concentrations, do not have a significant effect on HPV-11 VLP disassembly. This was shown using both EGTA and EDTA, both well known chelators, alone and in combination with dithiothreitol. As discussed previously, this is surprising because chelating agents have been reported to be necessary in VLP disassembly for a related papovavirus.

Furthermore, it has been found that carbonate buffer (0.2 M $NaHCO_3$ pH 9.6) caused significant disassembly of HPV-11 VLPs. However, unlike disassembly induced by prolonged exposure to sulfhydryl reducing agents, it was not possible to reassemble carbonate-treated VLPs. It is hypothesized that the carbonate treatment partially denatured the L1 protein. This demonstrates that only those methods (such a prolonged exposure to effective concentrations of sulfhydryl reducing agents) which disassemble VLPs while retaining correctly-folded L1 protein structure will produce material which is competent to reassemble into full-size, soluble, VLPs.

As noted, the subject disassembly of HPV-11 VLPs results in capsomeres of high homogeneity that present conformational, neutralizing epitopes as demonstrated by their reactivity with conformational and neutralizing monoclonal antibodies produced against the particular papillomavirus (HPV-11 exemplified). Moreover, under optimal conditions, the subject method results in a composition wherein VLPs appear to be totally broken down to capsomeres. Conversely, the subject disassembly of HPV-$16_{Tr}$ VLPs appears to result in a mixture of capsomeres, smaller L1 oligomers and L1 monomers. However, this mixture of L1 oligomers is also capable of quantitative reassembly. This indicates that the subject method yields correctly-folded L1 protein, in the form of capsomeres, smaller L1 oligomers, or L1 monomer, which is competent for VLP reassembly.

As discussed, a particular advantage of the invention is that these capsomeres can then quantitatively assemble into VLPs simply by removal of the reducing agent solution. Removal of reducing agent may be accomplished by various methods, e.g., dialysis or column chromatography. Alternatively, addition of excess oxidants can potentially promote the reformation of the appropriate disulfide bonds, leading to VLP reassembly. As discussed above, reassembly is affected by the structural integrity of the correctly-folded L1 protein starting material. Also, the solubility of the starting material affects reassembly, as aggregated material will not reassemble quantitatively.

In general, reassembly will be effected by removal of the sulfhydryl reducing agent or addition of oxidants and exposure of correctly-folded L1 protein starting material to higher ionic strength conditions, e.g., at least about 0.5 or higher. Higher salt concentrations function to stabilize the VLPs. However, the addition of chelating agents has the opposite effect, i.e., it moderately inhibits reassembly.

Surprisingly, such reassembly results in VLPs which are much more homogenous in particle size than the original VLP starting material. This was demonstrated by comparison of the starting VLP material and reassembled VLP product on 10–65% linear sucrose gradients, and by examination under the electron microscope. Predominantly, particles in the range of full-size VLPs were detected, averaging 56.5±7.0 nm with very few partially assembled VLPs or smaller complexes apparent. Also, the yields are very high, averaging about 80–90% in terms of ratio of total L1 protein from starting material to reassembled VLPs using optimal reassembly conditions. Essentially, all of the disassembled starting material appear to reform soluble, filterable, full-size VLPs. Also, these VLPs exhibit conformational, neutralizing epitopes found on the surface of authentic papillomavirus virions and elicit neutralizing antibodies as potently as the VLP starting material.

While these results are novel and unexpected, it is nevertheless expected, based on the teachings of the application, that one skilled in the art may achieve even greater VLP yields by varying protein concentration, pH, ionic strength and/or kinetics.

As discussed, the present invention further provides methods for producing papillomavirus VLPs which have encapsulated therein a desired moiety or moieties. This will generally be accomplished by the following steps:

(i) obtaining VLPs of a desired papillomavirus, which are constituted of L1 or a combination of L1 and L2 proteins;

(ii) disassembling such VLPs by contacting such VLPs with a solution containing a high concentration of sulfhydryl reducing agent having an ionic strength which is at most 0.5;

(iii) contacting the disassembled VLPs with a solution containing a moiety to be encapsulated therein, and optionally also containing purified L2 protein (e.g., if the disassembled VLPs did not comprise L2 protein); and (iv) reassembling said disassembled VLPs by removal of the sulfhydryl reducing agent or by addition of excess oxidant, thereby producing VLPs containing the desired moiety(ies).

The disassembly and assembly steps are conducted as described previously, i.e., disassembly is effected by use of high concentrations of sulfhydryl reducing agents, typically at least 1% by weight, or higher, and for prolonged periods, i.e., at least 2 hours, and typically longer, e.g., at least 16 hours. As discussed, the exposure time and concentration of reducing agent are affected by the type of papillomavirus VLPs, the host cell system in which they are produced, mutations within the L1 protein (e.g., C-terminal truncations), level of purity, whether aggregates are present, and potentially whether the VLPs are comprised of L1 or a combination of L1 and L2. Reassembly occurs upon the removal or oxidation of the sulfhydryl reducing agent.

As discussed previously, while it is reasonable to assume that VLPs comprised of L1 and L2 will disassemble under similar conditions as L1 based VLPs, the L2 protein may serve a stabilizing function. Therefore, disassembly of VLPs comprised of L1 and L2 may potentially require higher reducing agent concentrations, more prolonged exposure thereto reduced ionic strength, elevated pH or a combination thereof. Alternatively, VLPs constituted entirely of PV L1 proteins may be disassembled as taught herein, and purified L2 protein (produced by recombinant methods) may be added during the reassembly step.

The moieties that may be encapsulated in the VLPs include therapeutic and diagnostic moieties, e.g., nucleic acid sequences, radionuclides, hormones, peptides, antiviral agents, antitumor agents, cell growth modulating agents, cell growth inhibitors, cytokines, antigens, toxins, etc.

The subject VLPs, which contain a desired moiety encapsulated therein, upon administration to a desired host, preferably human, should be taken up by cells normally infected by the particular papillomavirus, e.g., epithelial cells, keratinocytes, etc., thereby providing for the potential internalization of said encapsulated moiety into these cells. This may facilitate the use of the subject VLPs for therapy (as opposed to prophylatics) because it enables the delivery of a therapeutic agent into a desired cell site, e.g., a cervical cancer site. Given the fastidiousness of PVs in general, this may provide a highly selective means of delivering desired moieties to target cells. For example, it may provide a means of delivery of nucleic acid sequences, e.g., a DNA encoding a therapeutic polypeptide, or an antisense sequence.

The moiety or moieties encapsulated, of course, should not adversely affect VLP assembly and/or stability. This may be determined by producing VLPs containing the desired moiety and assessing its effects, if any, on VLP assembly and/or stability.

In the case of DNAs or RNAs, the encapsulated nucleic sequence can be up to 8 kilobases, the size of the PV genome. However, typically the encapsulated sequences will be smaller, e.g., on the order of 1–2 kilobases. Typically, these DNAs will encode a desired polypeptide, e.g., therapeutic polypeptide, such as an enzyme, hormone, growth factor, etc. This sequence will further be operably linked to sequences that facilitate the expression thereof in the targeted host cells.

Another application of VLPs containing encapsulated DNAs are as "pseudovirions". In this regard, numerous papillomaviruses, including those involved in human diseases, are rare, cannot be propagated readily in vitro and cannot be easily purified from human cell sources in amounts that facilitate the use thereof in antibody neutralization assays. This is problematic, as it prevents or makes difficult evaluating the feasibility of vaccines or therapeutics for protection against these specific HPV viruses. Examples of HPV types for which no stocks are currently available include HPV-31, 33, 35, and 45.

The present invention should obviate or at least reduce such problems. Essentially, "pseudovirions" will be constructed corresponding to these viruses which comprise VLPs which are constituted of L1 or a combination of L1 and L2 proteins of the particular PV, and further encapsulated therein part of the genome of said papillomavirus or a DNA encoding a selectable marker.

This pseudovirion will be used in an in vitro cell "infectivity" assay to evaluate efficacy of corresponding VLP vaccines. Essentially, this will be effected by contacting cells with such pseudovirions. These pseudovirions should bind such cells and provide for the insertion of said DNA. Thereafter, insertion of said DNA may be evaluated by known methods, e.g., PCR hybridization methods, or based on the expression of the selectable marker, e.g., β-galactosidase.

This will be effected both in the presence and absence of antibodies generated against L1 or L2 proteins specific to the particular HPV. If insertion is inhibited, as determined, e.g., based on reduced expression of the selectable marker, this is an indication that the L1 or L2 protein elicited production of virus-neutralizing antibodies.

The present invention is applicable for producing VLPs for any papillomavirus and in particular any human papillomavirus. Many HPV L1 and L2 DNAs have been reported in the literature and are publicly available (see, e.g., Baker, Sequence Analysis of Papillomavirus, *Genomes*, pp. 321–384; Long et al, U.S. Pat. No. 5,437,931, Cole et al, *J. Mol Biol.*, 193:599–608 (1987); Danos et al, *EMBO J.*, 1:231–236 (1982); Cole et al *J. Virol.*, 38(3):991–995 (1986)). Also, it is well known that HPV L1 DNAs exhibit significant homology. Therefore, a desired HPV L1 DNA can easily be obtained, e.g., by the use of a previously reported HPV L1 DNA or a fragment thereof as a hybridization probe or as a primer during polymerization chain reaction (PCR) amplification. Indeed, numerous HPV L1 DNAs have been cloned and expressed.

Preferably, the HPV L1 DNA said in the subject invention will be derived from an HPV which is involved in cancer or condylomata acuminata, e.g., HPV-16, HPV-18, HPV-31, HPV-33, HPV-35, HPV-39, HPV-45, HPV-51, HPV-52, and HPV-56 are involved in cancer, and HPV-6, HPV-11, HPV-30, HPV-42, HPV-43, HPV-44, HPV-54, HPV-55, and HPV-70, are involved in warts. However, the subject homogeneous VLPs may be produced from any desired HPV L1 DNA.

In general, the selected HPV L1 and optionally L2 sequences will be expressed in a desired recombinant host cell system, and used to produce HPV VLPs for disassembly.

The selected host and expression vector will be cultured under conditions that favor the production of VLPs. This will largely depend upon the selected host system and regulatory sequences contained in the vector, e.g., whether expression requires induction. After expression, the HPV VLPs will be extracted from the host cells. The means of extraction will also depend to some extent on the host/vector system.

For example, if an intracellular expression vector is selected, the host cells will need to be lysed and the HPV VLPs recovered from the lysate. By contrast, if the expression vector contains sequences that facilitate secretion, HPV VLPs can be recovered directly from the culture medium. Methods for recovery of heterologous proteins from recombinant host cells and culture medium are well known in the art.

HPV L1 sequences may be expressed in any host cell that provides for the expression of recoverable yields of HPV VLPs. Suitable host systems for expression of recombinant proteins are well known and include, by way of example, bacteria, mammalian cells, yeast, and insect cells. A preferred expression system comprises the baculovirus/insect cell system used in the examples as this system provides for high protein yields. However, HPV L1 and L2 proteins can be produced in other systems, in particular bacteria and yeast.

Suitable vectors for cloning of expression of the subject HPV L1 encoding DNA sequences are well known in the art and commercially available. Further, suitable regulatory sequences for achieving cloning and expression, e.g., promoters, polyadenylation sequences, enhancers and selectable markers are also well known. The selection of appropriate sequences for obtaining recoverable protein yields is routine to one skilled in the art.

VLPs have reported application in HPV prophylactic vaccines and diagnostics. Capsomeres produced by disassembly may also be useful, as it has been discovered that they present conformational neutralizing epitopes and induce neutralizing antibodies. The subject VLPs may be advantageous thereto because of their enhanced homogeneity, and potentially, stability.

As discussed, the present invention should be broadly applicable to any HPV L1 sequence. There are a variety of HPV types known in the art. Further, particular types of HPVs are associated with particular infections such as flat warts, cutaneous warts, epidermodysplasia verruciformis, lesions and cervical cancer. Over 60 different HPV types have been identified in clinical lesions by viral nucleotide sequence homology studies. See, for example, Jenson et al, In: Belshe, R. ed., Textbook of human virology, Second Edition, MASS:PSG, 1989:951 and Kremsdorf et al, *J. Virol.*, 52:1013–1018 (1984). The HPV type determines, in part, the site of infection, the pathological features and clinical appearance as well as the clinical course of the respective lesion.

Because it is believed that there is little or no cross-immunity for HPV types and immunity to infection is HPV type-specific, it will be necessary to produce recombinant HPV VLPs for each specific HPV type upon which protection or treatment is needed. However, due to the homology between the L1 proteins and genes, hybridization techniques can be utilized to isolate the particular L1 gene of interest. Nucleotide probes selected from regions of the L1 protein which have been demonstrated to show sequence homology, can be utilized to isolate other L1 genes. Methods for hybridization are known in the art (see, for example, *Nucleic Acid Hybridization, A Practical Approach*, IRL Press, Washington, D.C. (1985); *Molecular Cloning, A Laboratory Manual*, Maniatis et al, eds., Cold Spring Harbor Laboratory, Cold Spring Harbor, N.Y. (1982); and *Molecular Cloning, A Laboratory Manual*, Sambrook et al, eds., Cold Spring Harbor Laboratory, Second Edition, Cold Spring Harbor, N.Y. (1989)). Alternatively, PCR methods can be utilized to amplify L1 genes or gene fragments (see, e.g., U.S. Pat. Nos. 4,683,195; 4,683,202; and 4,800,159).

Virus particles can also be isolated for a particular papillomavirus type, the DNA cloned, and the nucleic acid sequences encoding L1 proteins isolated. Methods for isolation of viral particles and cloning of virus DNAs have been reported (see, e.g., Heilman et al, *J. Virology*, 36:395–407 (1980); Beaudenon et al, *Nature*, 321:246–249 (1986); Georges et al, *J. Virology*, 51:530–538 (1984); Kremsdorf et al, *J. Virology*, 52:1013–1018 (1984); Clad et al, *Virology*, 118:254–259 (1982); DeVilliers et al, *J. Virology*, 40:932–935 (1981); and European Patent Application 0,133, 123).

Alternatively, the L1 protein for a particular human papillomavirus can be isolated, the amino acid sequence determined and nucleic acid probes constructed based on the predicted DNA sequence. Such probes can be utilized in isolating the L1 gene from a library of the papillomavirus DNA (see, e.g., Suggs et al, *PNAS*, 78(11):6613–6617 (1981) and Young and Davis, *PNAS*, 80:1194 (1983)).

As discussed, VLP formation is somewhat sensitive to the cell type wherein expression is effected. Therefore, it is advantageous to select systems which produce large quantities of VLPs as the starting material for VLP disassembly. Generally, the expression system will comprise a vector having the L1 protein of interest and the appropriate regulatory regions as well as a suitable host cell.

As discussed, baculovirus vectors are preferably utilized. A baculovirus system offers the advantage that a large percentage of cells can be induced to express protein due to the use of infection rather than transfection techniques. While baculovirus is an insect virus and grows in insect cells (Sf9), these cells retain many of the eucaryotic mechanisms for processing of proteins including glycosylation and phosphorylation which may be important for generating proteins of appropriate conformation. Baculovirus vector systems are known in the art (see, e.g., Summers and Smith, *Texas Agricultural Experimental Bulletin*, No. 1555 (1987); Smith et al, *Mol. Cell Biol.*, 3:2156–2165 (1985); Posse, *Virus Research*, 5:4359 (1986); and Matsuura, *J. Gen. Virol.*, 68:1233–1250 (1987)). Also, it has been reported that baculovirus-infected cells express HPV L1 proteins exhibiting the appropriate conformation.

For expression in an appropriate expression system, an L1 gene or modified L1 gene is operably linked into an expression vector and introduced into a host cell to enable the expression of the L1 protein by that cell. The gene with the appropriate regulatory regions will be provided in the proper orientation and reading frame to allow for expression. Methods for gene construction are known in the art (see, in particular, *Molecular Cloning, A Laboratory Manual*, Sambrook et al, eds., Cold Spring Harbor Laboratory, Second Edition, Cold Spring Harbor, N.Y. (1989)), and the references cited therein.

A wide variety of transcriptional and regulatory sequences may be employed. The signals may be derived from viral sources, where the regulatory signals are associated with a particular gene which has a high level of expression. That is, strong promoters, for example, of viral or mammalian sources, will be utilized. In this manner, the optimum conditions for carrying out the invention include the cloning of the L1 gene into an expression vector that will overexpress conformationally-dependent virus-neutralizing epitopes of the L1 protein in transfected or infected target cells.

The suitability of the HPV VLPs produced according to the invention as vaccines or as diagnostic agents is confirmed by reaction with antibodies or monoclonal antibodies which react or recognize conformational epitopes present on the intact virion and based on their ability to elicit the production of neutralizing antiserum. Suitable assays determining whether neutralizing antibodies are produced are known to those skilled in the art. This is an essential characteristic of HPV VLPs which are to be used in HPV vaccines. In this manner, it can be verified whether the HPV VLPs will elicit the production of anti-HPV neutralizing antibodies. Thus, other expression vectors and expression systems can be tested for use in the invention.

As discussed, the VLPs of the present invention can be utilized to detect, diagnose, serotype, and treat papillomavirus infection. When used for diagnosis or serotyping, VLPs according to the invention may be labeled using any of a variety of labels and methods of labeling. Examples of types of labels which can be used in the present invention include, but are not limited to, enzyme labels, radioisotopic labels, non-radioactive isotopic labels, fluorescent labels, toxin labels, and chemiluminescent labels.

Examples of suitable enzyme labels include malate hydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholineesterase, etc.

Examples of suitable radioisotopic labels include $^{3}$H, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{211}$At, $^{212}$Pb, $^{47}$Sc, and $^{109}$Pd.

Examples of suitable fluorescent labels include a $^{152}$Eu label, a fluorescein label, an isothiocyanate label, a rhodamine label, a phycoerythrin label, a phycocyanin label, an allophycocyanin label, an o-phthaldehyde label, a fluorescamine label, etc.

Examples of suitable toxin labels include diphtheria toxin, ricin, and cholera toxin. Examples of chemiluminescent labels include a luminal label, an isoluminal label, an aromatic acridinium ester label, an imidazole label, and acridinium salt label, an oxalate ester label, a luciferin label, a luciferase label, an aequorin label, etc.

Those of ordinary skill in the art will know of other suitable labels which may be employed in accordance with the present invention. The binding of these labels to VLPs can be accomplished using standard techniques commonly known to those of ordinary skill in the art. Typical techniques are described by Kennedy et al, *Clin. Chim. Acta*, 70:1–31 (1976), and Schurs et al, *Clin. Chim. Acta*, 81:1–40 (1977). Coupling techniques mentioned in the latter are the glutaraldehyde method, the periodate method, the dimaleimide method, the m-maleimidobenzyl-N-hydroxysuccinimide ester method, all these methods incorporated by reference herein.

The detection of the anti-HPV antibodies using the subject VLPs can be improved through the use of carriers. Well-known carriers include glass, polystyrene, polypropylene, polyethylene, dextran, nylon, amylases, natural and modified celluloses, polyacrylamides, agaroses and magnetite. The nature of the carrier can be either soluble to some extent or insoluble for the purposes of the present invention. Those skilled in the art will note many other carriers suitable for binding proteins, or will be able to ascertain the same by use of routine experimentation.

The most important aspect of the present invention, however, involves the development of PV vaccines. The vaccines of the invention will contain an amount of the subject HPV VLPs sufficient to induce formation of neutralizing antibodies in the host contained in a pharmaceutically acceptable carrier.

Administration of the subject VLP-containing vaccines may be effected by any pharmaceutically acceptable means, e.g., parenterally, locally or systemically, including by way of example, oral, intranasal, intravenous, intramuscular, and topical administration. The manner of administration depends on factors including the natural route of infection. The dosage administered will depend upon factors including the age, health, weight, kind of concurrent treatment, if any, and nature and type of the particular human papillomavirus. The vaccine may be employed in dosage form such as capsules, liquid solutions, suspensions, or elixirs, for oral administration, or sterile liquid formulations such as solutions or suspensions for parenteral or intranasal use. An inert, immunologically acceptable carrier is preferably used, such as saline or phosphate-buffered saline.

The vaccines will be administered in therapeutically effective amounts. That is, in amounts sufficient to produce a protective immunological response. Generally, the vaccines will be administered in dosages ranging from about 0.1 mg protein to about 20 mg protein, more generally about 0.001 mg to about 100 mg protein. Single or multiple dosages can be administered.

The method of the present invention makes possible the preparation of HPV VLPs containing vaccines for preventing papillomavirus infection. Further, by following the methods of the invention, vaccines for any of human specific papillomavirus can be made.

As more than one PV type may be associated with PV infections, the vaccines may comprise stable HPV VLPs derived from more than one type of PV. For example, as HPV 16 and 18 are associated with cervical carcinomas, therefore a vaccine for cervical neoplasia may comprise VLPs of HPV 16; of HPV 18; or both HPV 16 and 18.

In fact, a variety of neoplasia are known to be associated with PV infections. For example, HPVs 3a and 10 have been associated with flat warts. A number of HPV types have been reported to be associated with epidermodysplasia verruciformis (EV) including HPVs 3a, 5, 8, 9, 10, and 12. HPVs 1, 2, 4, and 7 have been reported to be associated with cutaneous warts and HPVs 6b, 11a, 13, and 16 are associated with lesions of the mucus membranes (see, e.g., Kremsdorf et al, *J. Virol.*, 52:1013–1018 (1984); Beaudenon et al, *Nature*, 321:246–249 (1986); Heilman et al, *J. Virol.*, 36:395–407 (1980); and DeVilliers et al, *J. Virol.*, 40:932–935 (1981)). Thus, the subject vaccine formulations may comprise a mixture of reassembled VLPs derived from different HPV types depending upon the desired protection.

As indicated, the HPV VLPs of the invention can also be utilized for serotyping and for incorporation in serotyping kits.

For serological testing, the kits will comprise the subject HPV VLPs and means for detection such as enzyme substrates, labelled antibody, and the like.

Having now generally described the invention, the following examples are offered by way of illustration and not intended to be limiting unless otherwise specified.

EXAMPLES

The following materials and methods were used in the Examples.

Materials and Methods

HPV-11 VLPs

For use in studies of VLP-disassembly and reassembly using pure protein, HPV-11 L1 proteins were heterologously expressed in *Trichoplusia ni* (High Five®) cells infected with recombinant baculovirus encoding the complete L1 open reading frame downstream of the polyhedrin promoter as described. (Ghim et al, In M. A. Stanley (ed.) Immunology of human papillomaviruses, Plenum, New York, p. 147–153 (1993)). Cells were harvested approximately 72 hours post-infection, pelleted by centrifugation, and frozen. For preparation of VLPs, the cell paste was resuspended in homogenization buffer (20 mM $NaH_2PO_4$, 150 mM NaCl, pH 7.4, containing 10 µg/ml leupeptin, 1 µg/ml aprotinin, and 1 µg/ml pepstatin A) and lysed in a microfluidizer (Microfluidics model HC8000/3A). The homogenized lysate was then centrifuged at 100,000×g for 90 minutes and the pellet containing HPV-11 VLPs was resuspended in PBS containing CsCl (405 g/L). The clarified lysate was then centrifuged overnight at 83,000×g, and the VLP band was collected. The VLPs were diluted in PBS-0.5M NaCl, and layered over a two component step gradient composed of 30% and 63% sucrose. The gradients were centrifuged at 167,000×g for 3 hours, and the purified VLP band was collected at the interface between the 30% and 63% sucrose solutions. The VLPs were then dialyzed into selected buffers (either PBS, or PBS with NaCl added to a final concentration of 0.3 M or 0.5 M), and stored at 4° C. Protein concentration was determined by the Bradford assay (Bradford et al, *Anal. Biochem.*, 72: 248–254 (1976)) using bovine serum albumin as the reference protein, and L1 content was determined as described (Suzich et al, *Proc. Natl. Acad. Sci. USA*, 92: 11553–11557 (1995)). Starting with 25–30 g of wet cell paste, the above protocol yielded 15–25 mg of HPV-11 VLPs.

HPV-$16_{Tr}$ VLPs

For use in studies of VLP-disassembly and reassembly during purification, HPV-$16_{Tr}$ L1 proteins (composed of a mutated form of the HPV-16 L1 protein from which the C-terminal 34 amino acids have been deleted) were expressed in High Five® cells as described above. The cell paste was resuspended in extraction buffer (10 mM Tris, 1.0% Triton X-100, pH 6.0), mixed by stirring, and centrifuged briefly at 1,000×g. The pellet containing the HPV-$16_{Tr}$ VLPs was resuspended in 20 mM Tris, 0.1 M NaCl, pH 8.0 buffer, vortexed briefly, and centrifuged at 3,000×g for 30 min. The supernatant was collected, filtered through 0.45µ cellulose acetate syringe filters, and then incubated in the presence or absence of 4% βME for >2 hours at 4° C. prior to use in column purification trials. The clarified, filtered supernatant (+/−βME) was applied to different ion exchange resins at low conductivity values (5–15 milliohms), washed with several column volumes of equilibration buffer and eluted with a gradient of increasing NaCl. To test the utility of HIC to remove residual DNA and protein contaminants, the fractions containing the peak of the eluted L1 protein from IEC were pooled, adjusted to 0.7 M in ammonium sulfate and applied to an HIC column equilibrated in the same buffer. The column was washed with several column volumes of equilibration buffer, and then the L1 protein was eluted from the HIC column at lower ammonium sulfate concentration. The final products of the purification processes (+/−βME) were dialyzed extensively against PBS (0.5M NaCl), and compared in terms of purity, yield, and residual DNA. The appearance of the VLPs was characterized by electron microscopy and linear sucrose gradient analysis (see below).

Sucrose gradient centrifugation

Three types of sucrose gradients were used in these experiments. First, centrifugation on 30% sucrose cushions was used to identify conditions which favored the disassembly of VLPs into smaller, soluble components. 100–200 µl reaction mixtures containing VLPs (50–100 µg total protein) plus or minus potential disrupting agents were layered atop 5 ml centrifuge tubes filled with 4.8 ml of 30% sucrose (w/w in PBS-0.5M NaCl) and centrifuged at 197,000×g for 2 hours at 40° C. in a swinging bucket rotor. A 50 µl aliquot was taken from the very top of the tube, and mixed with 2×Laemmli sample preparation buffer (Laemmli, U.K., *Nature*, 227:680–685 (1970)). The remainder of the 30% sucrose cushion was removed by pipet, and the "pellet" (typically none was visible) was resuspended in 100 µl of 1×Laemmli sample preparation buffer. The presence of HPV-11 L1 protein at the top or bottom of the 30% sucrose cushion was then determined by SDS/PAGE, and the relative amount of L1 quantified by analysis of digitized gels. Second, the state of disassembled VLPs was determined by rate-zonal centrifugation through 5–20% linear sucrose gradients. Disassembled VLPs (100–200 µg total protein in 400 µl) were layered atop preformed 11.6 ml gradients composed of 5–20% sucrose (w/v in PBS-0.5M NaCl), and centrifuged at 111,000×g for 24 hours at 4° C. in a swinging bucket rotor. Fractions (0.5 ml) were collected across the gradient, and the "pellet" (typically none was visible) was resuspended in 0.5 ml of PBS by dounce homogenization. The position of HPV-11 L1 protein across the gradient was determined by immunoblotting. The gradients were calibrated using standard proteins with established sedimentation coefficients (*E. coli* β-galactosidase, 19 S; bovine liver catalase, 11.3 S; bovine serum albumin, 4.3 S), and the percentage of sucrose in the fractions was determined by refractometry.

Third, the state of initial, disassembled, and reassembled VLPs was determined by rate-zonal centrifugation through 10–65% linear sucrose gradients. HPV-11 L1 protein (100–200 μg total protein in 400 μl) in various states of assembly was layered atop preformed 11.6 ml gradients composed of 10–65% sucrose (w/v in PBS-0.5M NaCl), and centrifuged at 188,000×g for 2.5 hours at 40° C. in a swinging bucket rotor. The gradients were collected (in 1.0 ml fractions), analyzed, and calibrated as above, with parvovirus B19 (70 S) and HPV-18 L1 VLPs (160 S) used as additional calibration standards.

Gel Electrophoresis

SDS/PAGE

SDS/PAGE was performed largely according to the method of Laemmli (Laemmli, U. K., *Nature,* 227: 680–685 (1970)). Samples were mixed with sample preparation buffer, boiled for 2 minutes, briefly spun in a minifuge, and loaded onto 7.5% (FIG. 1) or 10% (FIGS. 2–4) minigels with a 4% stacking gel. Gels were run for approximately 1 hour at 20 mA, constant current at room temperature, and protein was visualized by staining with Coomassie brilliant blue R250.

Immunoblotting

Electroblots of HPV-11 L1 from SDS/PAGE gels were prepared largely according to the method of Towbin et al (*Proc. Natl. Acad. Sci. USA,* 76: 4350–4354 (1979)). The blots were blocked with 1% nonfat milk protein in PBS overnight at 4° C. The blots were probed with AU1 (Berkely Antibody Co.), a mouse monocional directed against a linear epitope on papillomavirus L1 proteins (25) for 90 minutes, washed with PBS, 0.1% Triton X-100, and then reblocked for 30 minutes. The blots were then incubated with HRP-labeled goat anti-mouse IgG (Southern Biotechnology Associates, Inc.) for 40 minutes, and washed as above. The blots were then developed with ECL Western blotting reagent (Amersham), and exposed to X-ray film.

Analysis of gels

The $M_r$ of monomeric and oligomeric L1 were determined from their $R_f$ values on 7.5% SDS/PAGE, in comparison to standard proteins (See, Jackowski et al, In T. E. Creighton (ed.), Protein structure: a practical approach, IRL Press, New York, p 1–21 (1989)). When indicated, gels were digitized on a Hewlett Packard Scanjet Plus flatbed densitometer, and the relative intensity of bands was determined using Scan Analysis software (Version 2.2; Specom Research).

Electron microscopy

Protein samples were allowed to settle on formvar-and carbon-coated copper grids (Electron Microscopy Sciences), blotted dry, and stained with freshly-filtered 2% phosphotungstic acid (pH 6.8). Grids were examined in a JEOL model 1005 transmission electron microscope at an accelerating voltage of 100 KV and photographed at nominal magnifications of 15–25,000×.

Enzyme-linked immunosorbent assay (ELISA)

HPV-11 L1 VLPs (0.5–1.0 mg/ml L1) in PBS-0.3 M NaCl were either stored without treatment at 4° C., or incubated overnight at 4° C. following addition of βME (to a final concentration of 5%) or 2.0 M carbonate buffer, pH 9.6 (to a final concentration of 200 mM carbonate). A portion of treated samples were then dialyzed against 4×IL PBS-0.5 M NaCl at 4° C. for ≧24 hrs. All samples were diluted to a concentration of 0.8 μg L1/ml and distributed into the wells of microliter plates (80 ng L1 per well). Untreated VLPs and dialyzed material were diluted into PBS. The sample treated with βME without subsequent dialysis was diluted into PBS containing 5% βME, and undialyzed sample incubated in 200 mM carbonate was diluted into 200 mM carbonate, pH 9.6. Following incubation at 37° C. for 1 hr, the plates were washed with PBS, 0.1% Tween −20 (PBS-Tw) and blocked with 5% nonfat milk protein in PBS. Monoclonal antibodies (AU1, or H11.F1 and H11.A3 purified from ascites purchased from Pennsylvania State University (Christensen et al, *J. Virol.,* 64:5678–5681 (1990)), were diluted in 1% nonfat milk in PBS and added to the wells. Following a 2 hr incubation at room temperature, the plates were washed with PBS-TW and HRP-labeled goat anti-mouse IgG was added. After 1 hr at room temperature, the plates were washed as above and developed with HRP substrate (Kirkegaard and Perry Laboratories). Optical density measurements were made at 405 nm at the 15 min endpoint. Averages of duplicate wells were calculated as the final optical density values.

HPV-11 Neutralization Assay

Antisera against original purified HPV-11 VLPs, and HPV-11 VLPs which were disassembled by prolonged exposure to sulfhydryl reducing agent and then reassembled upon removal of the reducing agent by dialysis, were generated in BALB/c mice (groups of 5). The mice were injected s.c. with 1 μg of VLPs adsorbed to 1 mg/ml alhydrogel adjuvant at weeks 0, 4, and 9, with terminal bleeds performed on week 13. To determine whether the antisera raised in the mice was able to neutralize HPV-11 virus, the ability of the antisera to block the expression of a specific HPV-11 spliced mRNA in a human cell line (HaCaT) was tested.

HaCaT, an immortalized human keratinocyte cell line (Boukamp et al, *J. Cell Biol.,* 106: 761–771 (1988)) were provided by Dr. Norbert Fusenig. Cells were grown to confluency in 154/HKGS (Cascade Biologics, Inc.) supplemented with penicillin (100 units/ml) and streptomycin (100 μg/ml) in 24 well plates. HPV-11$_{Hershey}$ stock virus, purchased from Dr. John Kreider (Kreider et al, *J. Virol.,* 61:590–593 (1987)), was sonicated for 25 sec on ice, diluted in 154/HKGS medium, and incubated for one hour at 37° C. Medium was aspirated from the HaCaT cells and 0.5 ml of diluted virus was added per well. As a control, one well of cells on each plate received 0.5 ml of medium without virus. For antibody-mediated neutralization, antisera were diluted in 154/HKGS and incubated with a fixed quantity at the HPV-11 stock virus in a final volume of 0.5 ml for one hour at 37° C. prior to addition to the HaCaT cells. Fresh medium was added to each well of cells four days post-infection, and on day six cells were harvested and total cellular RNA was prepared using Tri Reagent (Molecular Research Center, Inc.). Final RNA pellets were resuspended in 20 μl of DEPC-treated water and quantified by spectrophotometry.

The ability of the antisera to block the expression of HPV-11-specific spliced mRNA was determined by reverse-transcriptase (RT)-PCR. RT reactions were performed using a First Strand cDNA kit (Boehringer Mannheim) with 2 μg of total RNA as the template and oligo dT as the primer. Nested PCR was needed to detect HPV-11 E1ΛE4 cDNA. The first round of amplification was carried out with 25% of the cDNA from each RT reaction and 5'-TACAAGACCTTTTGCTCGGCACA-3" (located at bases 765–787 in the HPV-11 genomic sequence) as the forward outside primer and 5'-AAAGGCAGGAAAATAGCACAC-3' (located at bases 4088–4110 in the HPV-11 genomic sequence) as the reverse ouside primer for 30 cycles of PCR. Ten percent of the first round PCR mixture was used for nested reactions with 5'-ATATTGTGTGTCCCATCTGCG-3" (located at bases 792–812 as nested forward primer and 5'-CAGCAATTTGTACAGGCACTAC-3' (located at bases 3877–3898 in the HPV-11 genomic sequence) as the nested reverse primer for 30 cycles of PCR. First round and nested PCR reactions were set up with Hot Wax beads (1.5 mM) and pH 9.5 buffer (InVitrogen) with 200 μM dNTPs, 125 ng each forward and reverse primer, and 2.5 units of Taq polymerase (Perkin-Elmer) in a final volume of 50 μl. The temperature profile for both first round and nested PCR was 80° C./5 min, 95° C./30 sec, 72° C./30 sec, with a final extension at 72° C. for 10 min.

As a control to demonstrate that the assay was able to detect mRNa extracted from HaCat cells, all cDNA samples were used in separate PCR reactions with primers specific for spliced cellular β-actin mRNA as described and amplified as above (Smith et al, *J. Invest. Dermatol.*, 105: 1–7) (1995)).

All PCR products were separated by electrophoresis on a 2% agarose gel and visualized by ethidium bromide fluorescence.

Example 1

Quantitative Disassembly of HPV-11 VLPs

Figure 4A:
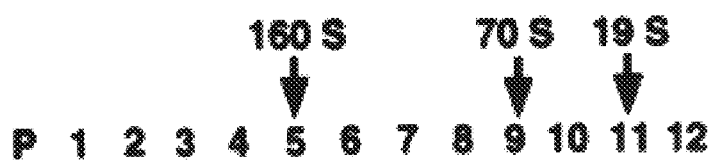
Figure 4A:
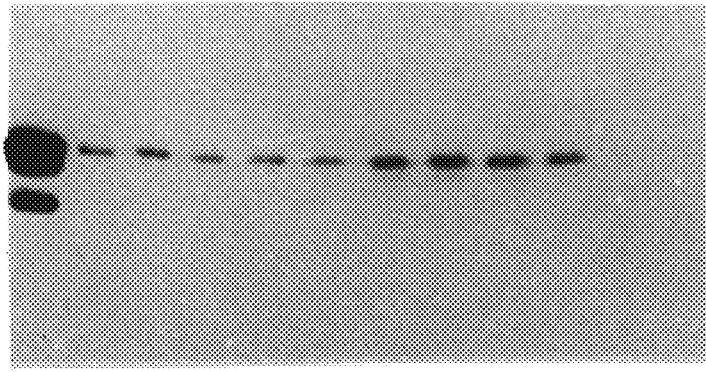
Figure 5A:
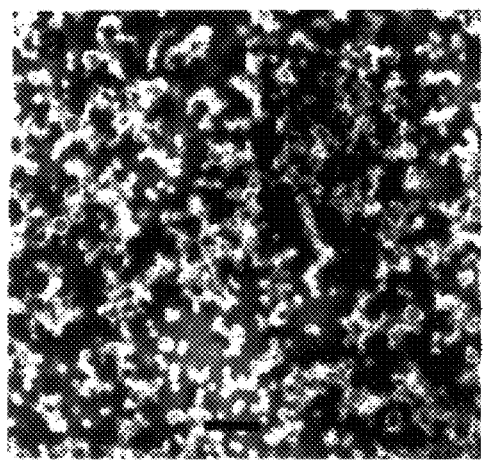

Relatively large quantities of HPV-11 L1 VLPs were prepared as starting material for the study of VLP disassembly and reassembly. HPV-11 L1 VLPs were isolated from recombinant baculovirus-infected High Five® cells by CsCl and sucrose gradient centrifugation. The calculated purity of these L1 preparations, based on densitometric analysis of SDS/PAGE, ranged between 70–90% (see FIG. 1, lane 2). In addition, in linear sucrose gradients most of the protein migrated as expected for a mixture of individual and clumped VLPs (FIG. 4a), and in the electron microscope a mixture of intermediate and full-size (50–55 nm) particles were apparent (FIG. 5a).

The covalent and non-covalent interactions which stabilize the assembled L1 VLPs are not entirely known, but earlier work on papillomavirus VLPs and related polyomavirus virions and VLPs suggested the importance of ionic strength, divalent cations (Brady et al, *J. Virol.*, 23:717–724 (1977); Salunke et al, *Biophys. J.*, 56:887–900 (1987), and disulfide bonds (Sapp et al, *J. Gen. Virol.*, 76:2407–2512 (1995); Volpers et al, *Virology*, 200:504–512 (1994)). In particular, Sapp and co-workers had demonstrated by immunoblotting that ~50 percent of the L1 protein of HPV-33 VLPs was disulfide-bonded into a range of larger oligomers with an apparent $M_r$ consistent with trimers of L1, and that mild reducing conditions partially broke down HPV-33 VLPs to the level of capsomeres (Sapp et al, *J. Gen. Virol.*, 76:2407–2412 (1995); Volpers et al, *Virol.*, 200:504–512 (1994)). In our studies, in the absence of reducing agents only a portion of the HPV-11 L1 protein migrated on SDS/PAGE with an apparent $M_r$ of 55,000 Da (FIG. 1, Lane 1). Approximately 40% (the percentage varied between different VLP preparations) of the L1 protein of HPV-1 VLPs was disulfide-bonded into larger oligomers (FIG. 1, Lane 1), with predicted $M_r$ values of approximately 144,000 Da (possibly L1 trimer) and 210,000 Da (possibly L1 tetramer). The L1 oligomers did not migrate as a single band, and appeared to be heterogeneous in size. The ~200,000 Da oligomer was also observed on immunoblots by Sapp and coworkers (Sapp et al, *J. Gen. Virol.*, 76:2407–2412 (1995); Volpers et al, *Virol.*, 200:504–512 (1994)), as part of a broad higher molecular weight band. These results indicate that a portion of the L1 proteins in HPV-11 VLPs are disulfide-linked into higher oligomers. To study the role of disulfide linkages and other interactions in VLP stability, a rapid screening assay for VLP disassembly was developed. Purified HPV-11 L1 VLPs, both before and after various treatments, were layered atop 30% sucrose cushions, centrifuged, and the distribution of L1 protein at the top and bottom of the 30% cushion was visualized by SDS/PAGE. Intact VLPs were expected to pellet through the 30% sucrose cushion; non-aggregated capsomeres and L1 monomer were expected to remain on the top of the cushion. An example of this assay is shown in FIG. 2. To quantitate the relative disposition of L1 protein, the gels were digitized, the total intensity of the L1 bands at the top and the bottom of the cushion was determined, and then the percentage of the L1 staining intensity found at either position was calculated. The results of a number of such determinations are tabulated in Tables 1 and 2. As demonstrated in FIG. 2, the purified VLP starting material sedimented through the 30% sucrose, as predicted, with no L1 apparent at the top. However, upon incubation with a high concentration of the reducing agent β-mercaptoethanol (βME), L1 protein was found largely at the top of the 30% sucrose cushion, indicating that the reducing agent had disassembled the HPV-11 VLPs to smaller, non-aggregated components. Interestingly, maximal disassembly of the VLPs typically required exposure to a very high concentration of reducing agent (in this instance 5%, or 713 mM, βME) for a relatively long duration (~16 hours at 4° C.). Lower concentrations of reducing agent or shorter durations of reduction were not as reliably effective at VLP disassembly. Addition of a low concentration of a chelating agent did not enhance disassembly (FIG. 2 and Table 1)

In addition to reductants, the other important variables for quantitative disassembly of VLPs were found to be the ionic strength during the disassembly reaction and the solubility of the VLP starting material. As observed earlier for polyomavirus virions, lower ionic strength conditions destabilize VLPs (Brady et al, *J. Virol.*, 23:717–724 (1977)), although Sapp et al (*J. Gen. Virol.*, 76:2407–2412 (1996)) reported that generation of HPV-33 capsomeres from VLPs was insensitive to salt concentration between 0.15M and 0.6 M NaCl. For HPV-11 VLPs, maximum disassembly (~90%) of VLPs exposed to 5% βME for 16 hours was observed at "physiological" ionic strength (i.e., 0.15 M NaCl), but became correspondingly less effective as the ionic strength was increased (Table 1). The stabilizing effect of increased ionic strength could be partially overcome by incubating the VLPs with reducing agents for longer durations or at elevated temperatures. However, while incubating the VLPs with 5% βME for 120 hours at 4° C., or for 24 hours at 24° C. increased the extent of disassembly to 60–70% at 0.5 M NaCl, disassembly was still far from complete (data not shown). Furthermore, for quantitative disassembly, the degree of aggregation of the VLP starting material was also important. In the experiments reported here, the VLP solutions were dialyzed into different ionic strength buffers and stored at 4° C. until use in disassembly trials. After several days, particularly at 0.15 M NaCl, the solutions became slightly cloudy, indicating some degree of aggregation (although little or no precipitate was observed). Treatment of the clouded VLP solutions with reducing agents did not yield the same degree of disassembly as was observed with the initial soluble VLP solution, indicating that the aggregated VLPs were resistant to disassembly. However, upon removal of the aggregated material (which ranged from 10–50% of the total VLPs depending on the age of the preparation) by filtration, the remaining soluble VLPs again could be disassembled to the same extent as the initial soluble VLP starting material.

Interestingly, even at high concentrations of chelators, chelation of cations did not significantly influence VLP disassembly. Dialysis of VLPs into 200 mM EDTA or EGTA buffers (PBS-0.3 M NaCl, pH 7.4) led to no apparent disassembly, and the addition of 10 mM dithiothreitol (DTT) to the dialysis buffers had little effect (Table 2). The inability of high concentrations of chelators to disassemble VLPs was confirmed by electron microscopic analysis, although EDTA (but not EGTA) appeared to swell the VLPs slightly (data not shown). Either these concentrations of chelator are insufficient to extract tightly bound, structurally-important ions, or cations are not essential to maintaining VLP structural integrity. Conversely, addition of a concentrated aliquot of $NaHCO_3$ buffer (pH 9.6) to a solution of VLPs, to a final concentration of 200 mM carbonate (in PBS-0.3 M NaCl), caused significant breakdown of the VLPs (Table 2). Addition of DTT (to a final concentration of 10 mM), did not further enhance carbonate-induced breakdown. Incubation of VLPs with 200 mM carbonate/10 mM DTT is commonly used to denature HPV virions or VLPs in ELISAs (Favre et al, *J. Virol.*, 15:1239–1237 (1975); Christensen et al, *J. Virol.*, 64:3151–3156 (1990); Christensen et al, *J. Gen. Virol.*, 75:2271–2276 (1994)). The effect of carbonate appears to be buffer specific, and not merely a function of pH, as incubation of HPV-11 VLPs with pH 9.6 glycine buffer (200 mM final concentration) caused very little VLP breakdown, as measured by the 30% sucrose cushion assay (Table 2). Similarly, Brady et al (*J. Virol.*, 23:717–724 (1977)), observed that carbonate buffer at alkaline pH, but not alkaline pH alone, dissociated polyomavirus virions. However, the specific effect of carbonate at pH 9.6 does not appear to be due to carbonate's potential chelating ability, as suggested by Brady et al (*J. Virol.*, 23:717– 724 (1977)), as 200 mM EDTA at pH 9.6 (+/±10 mM DTT) was completely ineffective at VLP disassembly (data not shown).

Example 2

Characterization of Disassembled HPV-11 VLPs

Figure 3A:
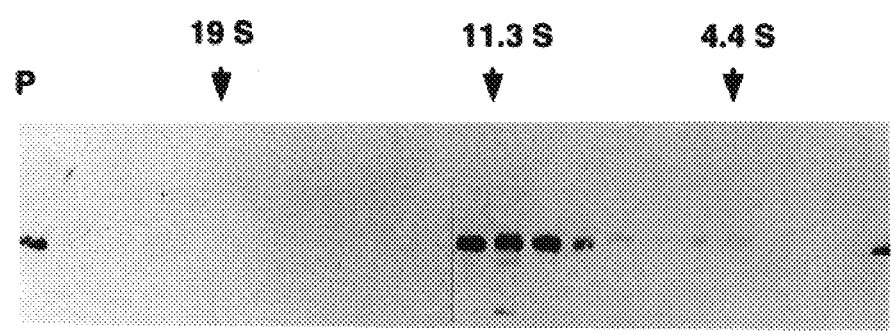
Figure 3B:
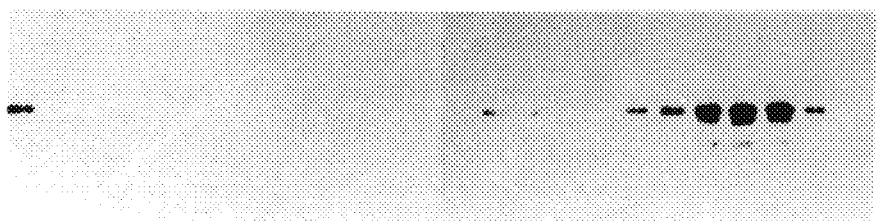

Following long-term exposure to high concentrations of reducing agent, the purified VLPs appear to be broken down to the level of capsomeres. As shown in FIG. 3a, the disassembled VLPs generated by incubation with 5% βME for 16 hours at 4° C. migrated on 5–20% linear sucrose gradients with an average sedimentation coefficient of 11.3±1.5 S (n=5), determined relative to sedimentation standards. Larger species, with a calculated sedimentation coefficient of 16–18 S (perhaps dimeric capsomeres), and even pelleted materials were occasionally observed. However, less than 10% of the L1 was detected at the top of the gradient (expected position for L1 monomer) or in the pellet (expected position for intact VLPs or aggregated capsomeres), suggesting that the purified VLP starting material was largely disassembled to the level of individual capsomeres upon prolonged reduction. This conclusion is supported by electron microscopic analysis of VLPs following prolonged incubation with 5% βME, which depicted a field of homogeneous capsomeres (FIG. 5b) averaging 9.7±1.2 nm (n=15) in diameter, with occasionally a few larger aggregated structures apparent (monomeric L1 would not be detected with this technique). The estimated capsomere diameter is slightly smaller than that observed by cryoelectronmicroscopy (11–12 nm) (Baker et al, *Biophys. J.*, 60:1445–1456 (1991); Hagensee et al, *J. Virol.*, 68:4503–4505, (1994); Belnap et al, *J. Mol. Biol.*, 259:249–263 (1996)), perhaps due to shrinkage during electron microscope grid preparation. The data demonstrated in FIGS. 3a and 5b indicate that prolonged exposure to high concentrations of reductants quantitatively disassembles purified, soluble VLPs to a homogenous population of capsomeres.

Figure 6A:
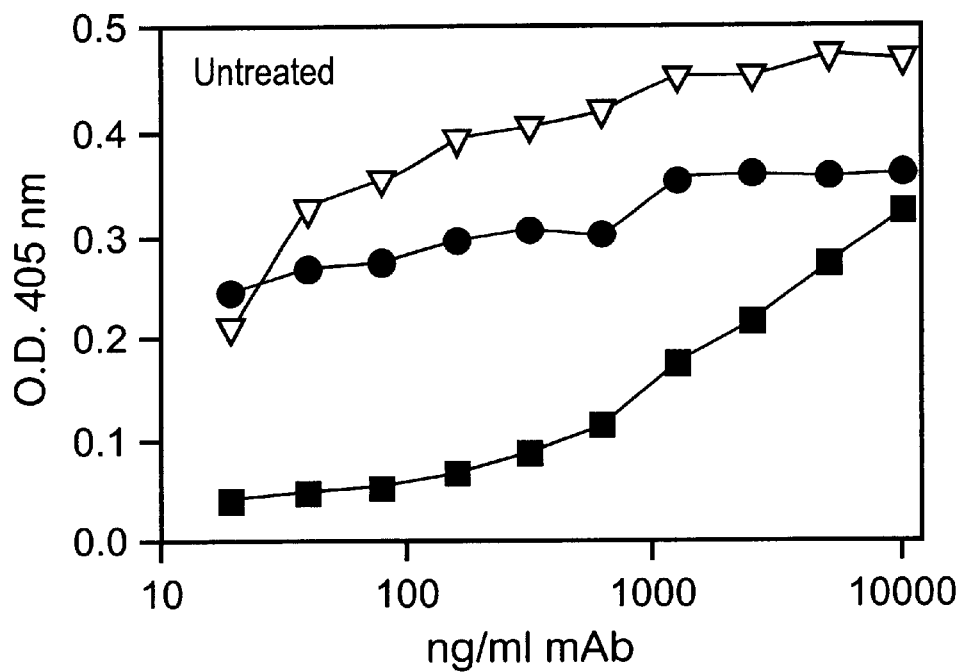
Figure 6B:
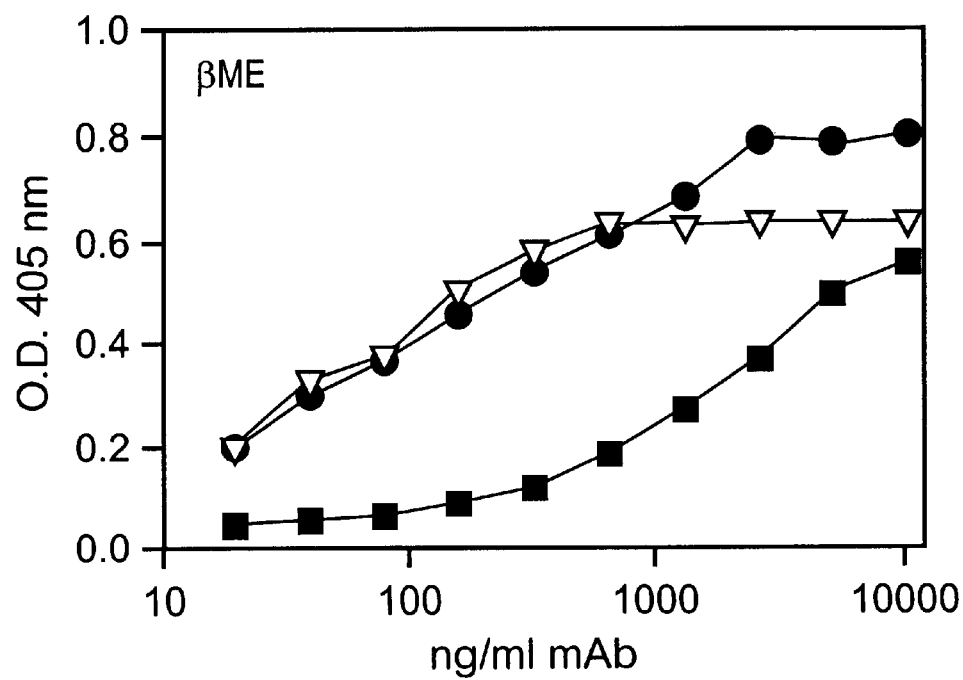

Capsomeres generated from HPV-11 VLPs upon long term exposure to high concentrations of reducing agent contain structural epitopes found on intact VLPs. A panel of HPV-11-specific monoclonal antibodies has been described which react with intact HPV-11 L1 VLPs but not with "denatured" L1. These monoclonals include H11.F1, which has been demonstrated to recognize a dominant neutralizing epitope on HPV-11 virions, and H11.A3, a distinct non-neutralizing structure-dependent antibody (Christensen and Kreider, *J. Virol.*, 64:3151–3156 (1990); Christensen et al, *J. Virol.*, 64:5678–5681 (1990)). As anticipated, H11.F1 and H11.A3 reacted strongly with the purified HPV-11 VLP starting material when analyzed by ELISA (FIG. 6a). However, these antibodies also reacted with capsomeres generated from the VLP starting material by exposure to reducing agent (FIG. 6b). Thus, capsomeres possess at least some of the structure-dependent epitopes found on the surface of intact VLPs and authentic virions, in agreement with studies performed by Li et al, (*J. Virol.*, 71:2988–2995 (1997)) on HPV-11 capsomeres expressed in *E. coli*. These results further demonstrate that monoclonal antibodies H11.F1 and H11.A3, while requiring a "native-like" conformation for binding, are not VLP-dependent as has been previously described (Ludmerer et al, *J. Virol.*, 71:3834–3839 (1997)).

By contrast, monoclonal antibodies H11.F1 and H11.A3 fail to recognize HPV 11 VLPs dissociated by treatment with carbonate buffer at pH 9.6 (data not shown; Christensen et al, *J. Gen. Virol.*, 75:2271–2275 (1994)). Carbonate treatment did not lead to a homogeneous solution of capsomeres, but instead appeared as an indistinct mixture of small objects, partially aggregated, when examined by electron microscopy (data not shown). This view was partially confirmed by analysis of carbonate-treated VLPs on 5–20% linear sucrose gradients, in which the L1 protein largely migrated at ~4 S, although a small population at 9–11 S was observed (FIG. 3b), in agreement with the effects of carbonate buffer (at pH 10.6, with 10 mM DTT) upon BPV virions (Favre et al, *J. Virol.*, 15:1239–1247 (1975)). Finally, while treatment with glycine buffer at pH 9.6 did not dissociate VLPs to smaller, individual particles (Table 2), it did have some effect. VLPs treated with a pH 9.6 glycine appeared in the electron microscope as a poorly-defined mixture of intact, and partially-broken down and aggregated VLPs (data not shown).

Example 3

Quantitative Reassembly of HPV-11 VLPs

Figure 4B:
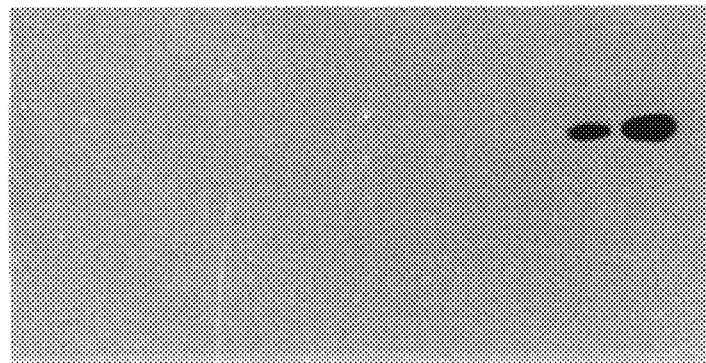
Figure 4C:
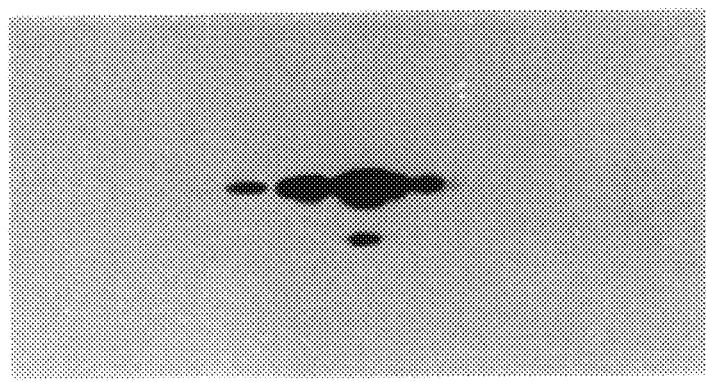
Figure 5C:
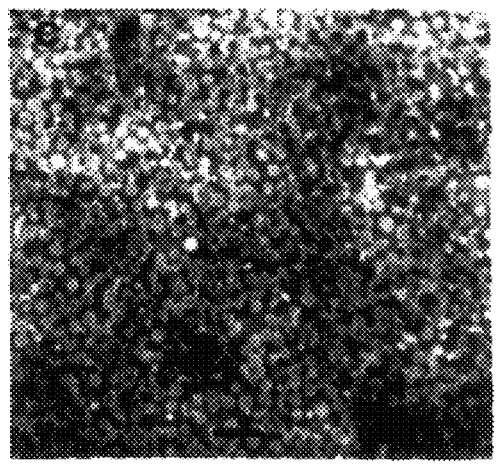
Figure 6C:
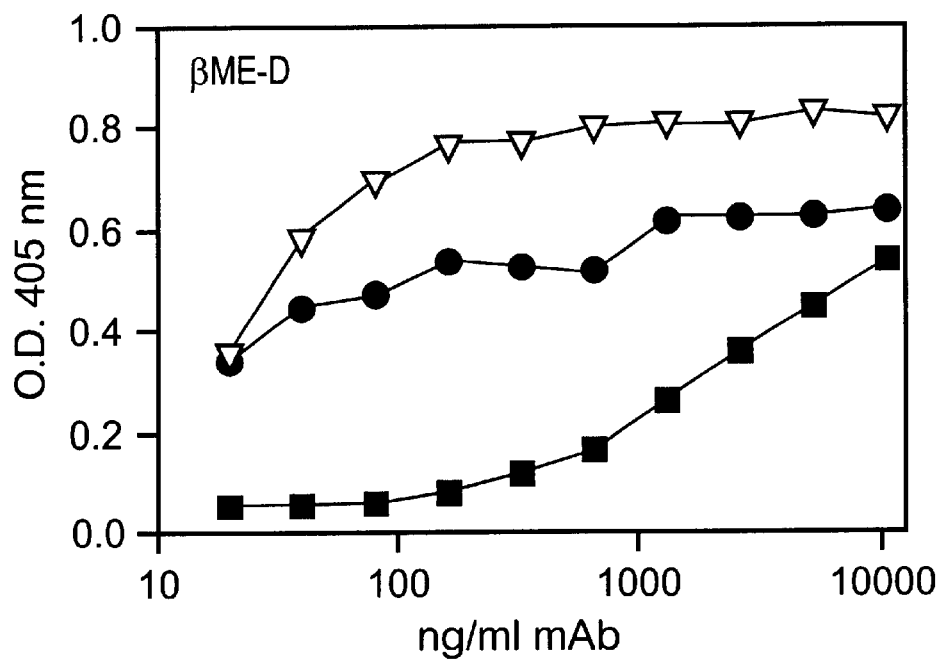

VLP reassembly from HPV-11 capsomeres occurred upon removal of reducing agent, either by dialysis or column chromatography. Starting with a homogeneous preparation of soluble capsomeres, prolonged dialysis in the absence of reducing agents consistently yielded a defined population of reassembled VLPs (FIGS. 4c and 5c,d). The reassembled VLPs retained the structural epitopes recognized by monoclonal antibodies H11.F1 and H11.A3 (FIG. 6c).

Figure 6D:
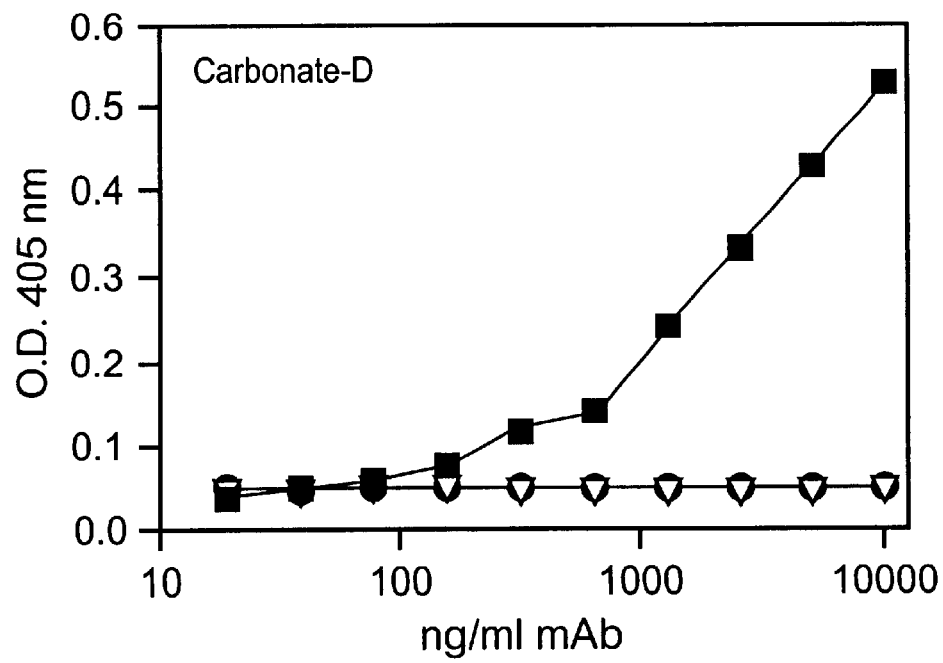

For reassembly, capsomeres (1–5 ml at 0.5–1.0 mg/ml total protein) were dialyzed versus 4×1 L PBS-0.5M NaCl at 4° C. for ≧24 hrs; the elevated salt concentration was designed to stabilize the VLPs. Whereas the addition of chelating agents did not appreciably enhance the ability of reducing agents to disassemble VLPs (Table 1), the presence of 2 mM EDTA moderately interfered with reassembly, yielding VLPs which migrated on a 10–65% linear sucrose gradient as a fairly discrete population of 150 S particles but appeared flattened and partially opened-up in the electron microscope (data not shown). Conversely, the addition of 1 mM $Ca^{2+}$ during the reassembly reaction caused the VLPs to adhere to one another, as shown by 10–65% linear sucrose gradient analysis, in which VLPs reassembled in the presence of calcium migrated entirely in the pellet. However, the presence of $Ca^{2+}$ did not otherwise appear to influence basic VLP morphology when examined in the electron microscope (data not shown). Finally, dialysis of carbonate-treated VLPs into PBS-0.5 M NaCl did not lead to the reassembly of VLPs. Instead, L1 protein remained as either small, soluble components or amorphous, aggregated precipitate, as evidenced by both electron microscopic and 10–65% linear-sucrose gradient analysis (data not shown). Dialysis of carbonate-treated VLPs failed to restore reactivity with structurespecific monoclonal antibodies H11.F1 and H11.A3 (FIG. 6d).

Characterization of Reassembled HPV-11 VLPs

Following removal of the reducing agent, capsomeres quantitatively reassembled into VLPs. Surprisingly, the reassembled VLPs were much more homogenous in particle size than the cesium and sucrose-gradient purified VLP starting material. When the three stages of the disassembly/reassembly reaction were compared by 10–65% linear sucrose gradients, the purified VLP starting material was distributed across the gradient, with many particles migrating to the position expected for intact VLPs (150–160 S), but with the majority of the protein further down the gradient and in the pellet (FIG. 4a). Similarly, when examined in the electron microscope (FIG. 5a), the VLP starting material was seen to be a mixture of different-sized particles, including full size, 50–55 nm diameter VLPs. It is possible that some disruption of VLPs occurred during extraction and purification, as linear sucrose gradient analysis of earlier stages of the purification process indicated a more homogeneous distribution of particle sizes (data not shown).

Figure 5B:
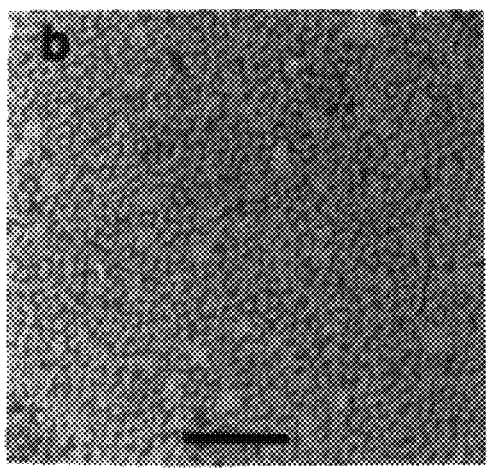
Figure 5D:
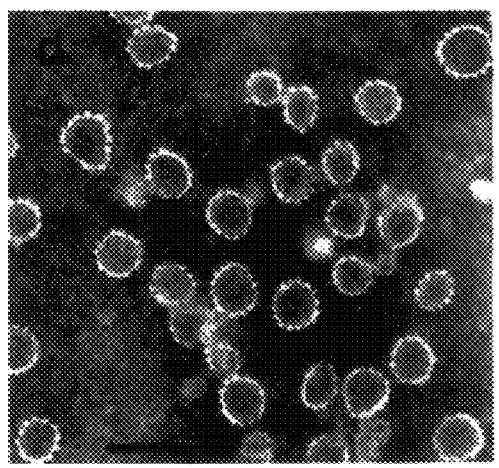

Upon long-term exposure to high concentrations of reducing agents, the VLPs were disassembled to capsomeres, as described above. Compared to the VLP starting material, the capsomeres migrated at the top of the 10–65% linear sucrose gradients (with little or no L1 detected in the pellet; FIG. 4b), and in the electron microscope appeared as an unbroken field of capsomeres (FIG. 5b).

Reassembly of the capsomeres yielded a homogeneous population of spherical, full-sized VLPs. The reassembled VLPs banded in the middle of the 10–65% linear sucrose gradients, with a predicted sedimentation coefficient of 150.4±4.6 S (n=7), with much less L1 detected either in the pellet or at the bottom of the gradient than was observed with the purified VLP starting material (FIG. 4c). The homogeneity of the reassembled VLPs was even more striking when examined in the electron microscope, as demonstrated in FIG. 5c,d. Predominantly particles in the range of full-size VLPs were detected, averaging 56.5±7.0 nm (n=15), with very few partially assembled VLPs or smaller complexes apparent. The yields of the reassembly process were also impressive (averaging 83% in terms of total L1 protein from starting material to reassembled VLPs under optimal disassembly conditions), as essentially all of the capsomeres appeared to reform soluble, filterable, full-size VLPs.

Example 4

Comparison of the Ability of Initial Purified HPV-11 VLPs and Reassembled HPV-11 VLPs to Generate Virus-neutralizing Antibodies In order for the reassembled VLPs to function sucessfully as vaccine candidates, it is essential that they retain the ability to elicit virus-neutralizing antibodies when injected into experimental animals. To test this, polyclonal antisera to both the initial, purified HPV-11 VLPs, and disassembled/reassembled HPV-11 VLPs, were generated in BALB/c mice as described in the Methods section. Each antisera was equally reactive against the corresponding immunogen when assayed in an ELISA format (data not shown). More importantly, when tested in the RT-PCR neutralization assay involving infectious HPV-11 virions (Smith et al, *J. Invest. Dermatol.,* 105:1–7 (1995)), post-immune reassembled HPV-11 VLP-specific polycolonal antisera exhibited a neutralization titer of $10^{-5}$–$10^{-6}$, equal to that obtained with the antisera generated against the initial, purified HPV-11 VLPs (FIG. 7). This demonstrates that the reassembled HPV-11 VLPs retain the highly immunogenic, capsid-neutralizing antigenic domain of HPV-11 virions, and have the potential to serve as vaccines for the prevention of genital HPV disease. Furthermore, given that the reassembled VLPs represent a homogeneous preparation of full-size VLPs (i.e., the size of infectious virus), it is possible that the reassembled VLPs will be more potent immunogens than the initial, purified VLPs, which are heterogeneous in size, a possibility currently being tested by dosing mice with decreasing amounts of initial and reassembled VLPs.

Example 5

Application of VLP Disassembly and Reassembly During the Purification of HPV VLPs As discussed above, conventional protein purification methods are not optimized for use with protein complexes the size of VLPs (20,000,000 Da, 55 nm diam. particles). In particular, the sheer size of VLPs dramatically lowers the capacity and utility of most chromatographic resins, as much of the reactive chemistry on the resin is sterically inaccessible to the VLP. However, this difficulty can potentially be avoided by disassembling crude VLPs extracted from cells, purifying the disassembled VLPs using standard methods, and reassembling the VLPs at the desired stage of purity. A second concern with VLP purification is contamination with residual DNA. In earlier work performed with purified HPV-11 VLPs, a certain level of background DNA persists which is not removed by treatment with DNAse, suggesting that the DNA is either encapsulated within the VLPs or very intimately associated with them. Disassembly of the VLPs should allow increased removal of contaminating DNA, an important consideration for any biological compound intended for clinical use.

To test this potential, HPV-$16_{Tr}$ VLPs were extracted from baculovirus-infected insect cells, and purified by conventional IEC and HIC chromatography as described in the Methods section, either in the absence of sulfhydryl reducing agent (intact VLPs), or in the presence of 4% βME (disassembled VLPs). In the latter case, the extracted VLPs were incubated with 4% βME for >2 hrs at 4° C. prior to chromatography on IEC and HIC columns, which were also equilibrated in βME. The final purified products of both purification procedures (i.e., in the presence or absence of sulfhydryl reducing agent) were dialyzed against 4×1 L PBS (0.5 M NaCl), and the purity, yield and residual DNA levels were determined. As shown in Table 3, a representative preparation purified in the absence of βME resulted in HPV-$16_{Tr}$ VLPs which were only about 60% pure (in terms of protein contamination) and contained levels of DNA higher than desired for human use. Conversely, three preparations of VLPs purified in the disassembled state were characterized by greater yields, significantly higher protein purity and substantially reduced residual DNA levels. The greater protein purity of VLPs purified in the disassembled state is readily apparent when analyzed by SDS/PAGE, as shown in FIG. 8. The size and homogeneity of the reassembled HPV-16$_{Tr}$ VLPs post purification has been more heterogeneous than that observed for reassembly of purified HPV-11 VLPs, but on average have been as homogeneous as HPV-16$_{Tr}$ VLPs purified without disassembly, and in some cases have formed uniformly homogeneous, full-sized VLPs, something we have never observed with HPV-16$_{Tr}$ VLPs purified without disassembly (data not shown).

There are interesting differences in the effects of prolonged treatment with sulfhydryl reducing agents between purified HPV-16$_{Tr}$ and HPV-11 VLPs. First, HPV-16$_{Tr}$ VLPs appear to disassemble quantitatively at lower levels of reducing agent and/or at shorter durations of exposure (data not shown). It is not apparent if this reflects a genuine difference between HPV-16 and HPV-11 VLPs, or if it is due to the C-terminal truncation of the HPV-16$_{Tr}$ L1 protein, as in preliminary trials we have observed that proteolytic trimming of the C-terminus of HPV-11 L1 protein also accelerates breakdown of VLPs in the presence of sulfhydryl reducing agent. A more interesting feature is that treatment of purified HPV-16$_{Tr}$ VLPs with sulfhydryl reducing agent appears to generate a mixture of capsomeres, smaller oligomers of the L1 protein and L1 monomer, on the basis of linear 5–20% sucrose gradient analysis of disassembled HPV-16$_{Tr}$ VLPs (FIG. 9). However, upon removal of the reducing agent by dialysis, this mix of small, soluble components is able to reassemble into intact VLPs with a yield of ~90%, as demonstrated by linear 10–65% sucrose gradient analysis (FIG. 10), and as confirmed by electron microscopic analysis (data not shown). These results demonstrate that VLPs can be disassembled to the level of capsomeres, or even smaller L1 oligomers, and still be competent to reassemble into intact, full-size VLPs, as long as the disassembly conditions generate soluble, correctly-folded L1 proteins.

TABLE 2-continued

Disassembly of HPV-11 L1 VLPs; Effects of chelators and buffers[a]

| Disassembly Condition | Top | Bottom |
| --- | --- | --- |
| 200 mM EGTA, pH 7.4 | 13 ± 11 | 87 ± 11 |
| 200 mM EGTA, 10 mM DTT | 11 ± 6 | 89 ± 6 |
| 200 mM NaHCO3, pH 9.6 | 81 ± 2 | 19 ± 2 |
| 200 mM NaHCO3, 10 mM DTT | 74 ± 11 | 26 ± 11 |
| 200 mM glycine, pH 9.6 | 11 ± 1 | 89 ± 1 |
| 200 mM glycine, 10 mM DTT | 41 ± 12 | 59 ± 11 |

[a]VLPs (0.5–1.0 mg/ml protein) were treated as indicated for 16 hours at 4° C., and the distribution of L1 across of 30% sucrose cushion was determined as described in the Methods section. Shown are the averages of duplicate determinations ± the range.

TABLE 2

Comparison of intact and dissambled HPV-16 $_{TR}$ VLP purification[a]

| Trial | Scale | Purity | Yield | DNA |
| --- | --- | --- | --- | --- |
| –βME | 24 g | 59% | 5.0% | 30 ng/100 μg L1 |
| +βME, Run 1 | 10 g | 85% | 10.8% | 5.3 ng/100 μ L1 |
| +βME, Run 2 | 10 g | 85% | 18.4% | 0.6 ng/100 μ L1 |
| +βME, Run 3 | 30 g | 81% | 6.1% | — |

[a]One purification of intact VLPs (–βME) and three purifications of disassembled VLPs (+βME, Runs 1–3) are compared and were prepared as described in the Methods section. Scale indicates the grams of cell paste used, purity was determined by densitometric analysis of SDS/PAGE of the final product compared to the amount present in the initial cell paste, and DNA was determined by the Threshold method and is reported per 100 μg of L1 protein, The expected maximal individual dose in humans.

CONCLUSIONS

Thus, the present invention provides precise conditions for the quantitative disassembly and subsequent reassembly of papillomavirus VLPs in vitro. As discussed, earlier attempts at papilloma VLP disassembly were to some extent

TABLE 1

Disassembly of HPV-11 L1 VLPS'; Effects of reducing agents[a]

| | 0.15M NaCl | | 0.3 m NaCl | | 0.5M NaCl | |
| --- | --- | --- | --- | --- | --- | --- |
| Disassembly Condition | Top | Bottom | Top | Bottom | Top | Bottom |
| Starting Material | 3.8 ± 0.7 | 96.3 ± 0.8 | 3.2 ± 1.4 | 96.8 ± 1.4 | 4.2 ± 0.3.4 | 95.9 ± 0.6 |
| 5% βME, 16 hr | 87.7 ± 3.2 | 12.4 ± 3.1 | 70.9 ± 12 | 29.1 ± 12 | 53.2 ± 6.8 | 46.8 ± 6.8 |
| 5 βME, 1 hr | 68.1 ± 11 | 31.9 ± 11 | 68.0 ± 10 | 32 ± 10 | — | — |
| 2% βME, 16 hr | 72.1 ± 2.7 | 27.9 ± 2.7 | 67.6 ± 21 | 32.3 ± 612 | — | — |
| 0.5% βME, 16 hr | 45.8 ± 18 | 54.2 ± 16 | 28.8 ± 16 | 71.2 ± 16 | — | — |
| 10 mM DTT, 16 hr | 44.5 ± 11 | 55.5 ± 11 | 43.8 ± 20 | 56.2 ± 20 | — | — |
| 10 mM DTT, 1 hr | 9.5 ± 6.4 | 90.5 ± 6.4 | — | — | — | — |
| 10 mM DTT, 5 mM EDTA, 16 hr | 55.9 ± 6.2 | 44.1 ± 6.2 | — | — | — | — |

[a]VLPs (0.5–1.0 mg/ml protein) were treated as indicated at 4° C., and the distribution of L1 across a 30% sucrose cushion was determined as described in the Methods section. Shown are the means of multiple determinations (n = 3 – 7) ± the standard deviation.

TABLE 2

Disassembly of HPV-11 L1 VLPs; Effects of chelators and buffers[a]

| Disassembly Condition | Top | Bottom |
| --- | --- | --- |
| 200 mM EDTA, pH 7.4 | 4 ± 3 | 96 ± 3 |
| 200 mM EDTA, 10 mM DTT | 10 ± 6 | 90 ± 6 | influenced by work performed upon polyomavirus, a related papovavirus, where it was shown that both reduction of disulfides and chelation of calcium ions were essential for virion disassembly (Brady et al, *J. Virol.,* (1977)). However, it was surprisingly found that the low levels of reducing agent (1–10 mM DTT) optimal for polyomavirus disassembly in the presence of low levels of chelating agents (e.g., 0.5–10 mM EDTA) were only slightly effective at disassembling papilloma VLPs (Table 1, Li et al, (Id.) (1997)), although partially-trypsinized HPV-11 L1 VLPs were dissociated by the above conditions (Li et al, (Id.) 1997)). However, Sapp and coworkers demonstrated that capsomeres could be generated from HPV-33 VLPs by treatment with reducing agent alone (20 mM DTT), although the extent of VLP breakdown was not determined (Sapp et al, (Id.) 1995)). In the experiments discussed previously, it was found that when examining disassembly by gradient analysis, it was necessary to test for the presence of L1 protein in the "pellet". In many cases, examination of fractions across the gradient would suggest that good breakdown had been achieved. However, examination of the pellet, even though none was visible, would indicate that a large percentage of the protein was still in the form of variably-sized VLPs or otherwise aggregated, as confirmed by electron microscopic analysis. The development of the 30% sucrose cushion assay allowed us to screen a number of disassembly conditions rapidly and identify those which consistently disassembled the VLPs to smaller, soluble components. It was found that quantitative disassembly to a homogeneous solution of individual capsomeres (for HPV-11 VLPs) or a mixture of capsomeres and correctly-folded smaller L1 oligomers and L1 monomers (HPV-$16_{Tr}$ VLPs) could be consistently achieved by extended treatment of non-aggregated VLPs with high levels of reducing agent in moderate to low ionic strength buffers.

As discussed, the observation that chelation of cations did not materially affect HVP-11 VLP disassembly was surprising as this is in contrast to earlier studies with polyomavirus which indicated that calcium chelation promoted virion disassembly and that added calcium could overcome the effect of chelators (Brady et al, (Id.) (1977)). Similarly, Montross et al, (Id.) (1991), observed that polyomavirus VLPs, which normally assemble only in the nucleus, could form in the cytoplasm following addition of a calcium ionophore, which presumably raised the cytoplasmic calcium concentration to the necessary level. However, calcium is apparently not important to HPV-11 L1 capsid stability. Conversely, treatment with carbonate buffer at alkaline pH did "disassemble" HPV-11 L1 VLPs, similar to results seen with polyomavirus virions (Brady et al, (Id.) 1977)). However, this treatment appears more severe, as VLPs could not be regenerated by dialysis into PBS-0.5 M NaCl following carbonate treatment.

HPV-11 VLP disassembly by carbonate treatment resulted in L1 protein which failed to react with structure-dependent, HPV-11-specific monoclonal antibodies. By contrast, disassembly of HPV-11 L1 VLPs by prolonged reduction resulted in capsomeres which possessed structure-specific epitopes found on the surface of both intact HPV-11 L1 VLPs and HPV-11 virions. These results support the idea that only correctly-folded L1 protein retains the ability to reassemble into VLPs.

In order to reassemble full-size VLPs efficiently in vitro, the results discussed herein indicate that the structural integrity, solubility and homogeneity of the starting material are significant. Following generation of a such a population of capsomeres (for HPV-11 VLPs) or a mixture of capsomeres and correctly-folded smaller L1 oligomers and L1 monomers (HPV-$16_{Tr}$ VLPs) by thiol reduction, reassembly occurs spontaneously upon removal of reducing agent. Reassembly was achieved by removing the sulfhydryl reducing agent, either by column chromatographic methods or by dialysis against a large excess of buffer, yielding a population of reassembled, full-sized VLPs more homogeneous in size than the VLP starting material. In earlier studies of polyomavirus, Salunke et al, (Id.) (1989) observed that VLP assembly from capsomeres yielded multiple, polymorphic icosahedral assemblies as a function of the assembly conditions (pH, ionic strength, and calcium concentration). Interestingly, the most consistently formed structure was a 24 capsomere icosahedron, as well as a 12 capsomere icosahedron, in addition to the 72 capsomere icosahedron of the viral capsid. The authors noted that disulfide bond formation might aid in polyoma VLP assembly but that it was not essential, as at high ionic strength (2 M ammonium sulfate) variably-sized capsids formed even in the presence of 15 mM βME. Similarly, Li et al, (Id.) (1997), have observed that column-purified HPV-11 capsomeres expressed in $E.\ coli$ have the capacity to form capsid-like structures in 1 M NaCl, again in the presence of 15 mM βME. However, while high ionic strength conditions apparently favor some degree of capsid formation, it is clear from our studies that at physiological ionic strength, disulfide binds are necessary to hold HPV-11 and HPV-$16_{Tr}$ L1 VLPs together.

Even given that the disassembly reactions were typically performed at 4° C. without agitation, it is interesting that maximal disassembly required prolonged exposure to very high levels of reducing agent. As we discussed previously, the most likely explanation is that the stabilizing disulfide bonds are buried and inaccessible, and that exposure of these bonds to solvent by local structural fluctuations is very infrequent.

The ability to reassemble full-sized VLPs in bulk opens a number of possibilities. As shown in FIG. 7, at high doses reassembled VLPs are capable of eliciting virus-neutralizing antibodies as the purified VLP starting material. We are currently testing the potency of the reassembled VLPs, to determine if they are as potent immunogens as the purified VLP starting material, which is less homogeneous in particle size. Whereas a number of different sized and shaped particles are observed in the nucleus of cells following infection in vivo (Kiselev et al, $J.\ Mol.\ Biol.,$ 40:155–171, (1969)), presumably only full-sized virus are productively infective. As discussed, the subject reassembled VLPs may potentially exhibit greater stability because of the subject method which provides for more uniform VLP particles. Further, as we discussed above, the reassembly reaction may potentially be further enhanced by varying protein concentration, pH, ionic strength and kinetics, both to optimize reassembly under a greater range of starting conditions. Finally, the subject invention enables the packaging of exogenous compounds within VLPs by performing the reassembly reaction in the presence of a concentrated solution of the selected compound. The subject invention, as discussed above, can be used to generate pseudovirions for use as surrogates for HPV virus types which are not currently available, or as a delivery system for drugs or other targeted compounds.

The invention may be embodied in other specific forms without departing from its spirit or essential characteristics. The described embodiments are to be considered in all respects only as illustrative and not restrictive, and the scope of the invention is, therefore, indicated by the appended claims rather than by the foregoing description. All modifications which come within the meaning and range of the lawful equivalency of the claims are to be embraced within that scope.

What is claimed is:

1. A method for producing papillomavirus virus-like particles comprised of L1 proteins or a combination of L1 and L2 proteins which have encapsulated therein at least one desired moiety comprising:

(i) disassembling a VLP composition comprising papillomavirus VLPs constituted of L1 proteins or a combination of L1 and L2 proteins by contacting such VLPs for a prolonged time period with a solution containing a high concentration of reducing agent;

(ii) contacting the resultant smaller, correctly-folded components with a solution containing at least one moiety that is to be encapsulated in reassembled papillomavirus VLPs, and optionally purified L2 protein; and (iii) removing said reducing agent or adding oxidants to provide for reassembly of said smaller, correctly-folded components into papillomavirus VLPs containing said moiety.

2. The method of claim 1, wherein the at least one moiety encapsulated in said reassembled VLPs is selected from the group consisting of nucleic acid sequences, radionuclides, anti-cancer agents, anti-viral agents, cell growth modulating agents, hormones, peptides, cytokines, antigens, toxins and mixtures thereof.

3. The method according to claim 2, wherein said moiety is a DNA.

4. The method according to claim 3, wherein said DNA encodes for a selectable marker.

5. The method according to claim 4, wherein said selectable marker is expressed in cells infected by said papillomavirus.

6. The method according to claim 3, wherein said DNA is at most about 8 kilobases.

7. A method of introducing a moiety into cells normally infected by papillomavirus comprising administering an effective amount of VLPs produced according to claim 1.

8. The method of claim 7, wherein said VLPs contain a DNA, antiviral agent or anti-cancer agent.

9. The method of claim 7, wherein said cells are epithelial cells or non-epithelial cells which are permissive for HPV VLP entry.

* * * * *

SEQUENCE LISTING

<160> NUMBER OF SEQ ID NOS: 4

<210> SEQ ID NO 1
<211> LENGTH: 23
<212> TYPE: DNA
<213> ORGANISM: Human Papillomavirus

<400> SEQUENCE: 1
tacaagacct tttgctgggc aca                                        23

<210> SEQ ID NO 2
<211> LENGTH: 21
<212> TYPE: DNA
<213> ORGANISM: Human Papillomavirus

<400> SEQUENCE: 2
aaaggcagga aaatagcaca c                                          21

<210> SEQ ID NO 3
<211> LENGTH: 21
<212> TYPE: DNA
<213> ORGANISM: Human Papillomavirus

<400> SEQUENCE: 3
atattgtgtg tcccatctgc g                                          21

<210> SEQ ID NO 4
<211> LENGTH: 22
<212> TYPE: DNA
<213> ORGANISM: Human Papillomavirus

<400> SEQUENCE: 4
cagcaatttg tacaggcact ac                                         22